US012702776B2

(12) United States Patent
Rapoport et al.

(10) Patent No.: US 12,702,776 B2
(45) Date of Patent: Aug. 11, 2026

(54) METHOD OF DRIVING A FORM OF RESPIRATORY THERAPY

(71) Applicant: Fisher & Paykel Healthcare Limited, Auckland (NZ)

(72) Inventors: David M. Rapoport, Auckland (NZ); Mark Renfrew Titchener, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 990 days.

(21) Appl. No.: 17/933,012

(22) Filed: Sep. 16, 2022

(65) Prior Publication Data

US 2023/0083767 A1 Mar. 16, 2023

Related U.S. Application Data

(63) Continuation of application No. 16/346,693, filed as application No. PCT/NZ2017/050139 on Oct. 30, 2017, now Pat. No. 11,478,595.

(Continued)

(51) Int. Cl.
*A61M 16/00* (2006.01)
*A61M 16/16* (2006.01)

(52) U.S. Cl.
CPC ...... *A61M 16/026* (2017.08); *A61M 16/0069* (2014.02); *A61M 2016/0027* (2013.01);

(Continued)

(58) Field of Classification Search
CPC ........................ A61M 16/026; A61M 16/0069
See application file for complete search history.

(56) References Cited

U.S. PATENT DOCUMENTS 4,773,411 A 9/1988 Downs
5,117,819 A 6/1992 Servidio et al.

(Continued)

FOREIGN PATENT DOCUMENTS

EP 3007753 B1 11/2018
WO WO 2015/131219 A1 9/2015

OTHER PUBLICATIONS

International Search Report in corresponding International Patent Application No. PCT/NZ2017/050139, dated Mar. 1, 2018, in 6 pages.

(Continued)

*Primary Examiner* — Margaret M Luarca
(74) *Attorney, Agent, or Firm* — Knobbe, Martens, Olson & Bear, LLP

(57) ABSTRACT

A method of controlling a medical device is disclosed for delivering respiratory therapy to a user to treat sleep-disordered breathing, for instance obstructive sleep apnea, Cheyne-Stokes respiration etc. by estimating the user's CO2 percentage or concentration from a dynamic lung model driven by an observed respiration signal. The estimated user's CO2 percentage or concentration can be used to predict breathing events, such as hypopnea and apnea. The predictive capacity can be used for adjusting the respiratory therapy as required or for applying a ramp cycle therapy, in an attempt to reduce the prevalence and adverse effects of the breathing events. In other examples a variable ventilation therapy is provided in which pressure is supplied between first and second pressures, with the pressure being increased over more than one breath, and then dropped relatively rapidly, for example during expiration of a single breath.

17 Claims, 12 Drawing Sheets

Related U.S. Application Data

(60) Provisional application No. 62/480,046, filed on Mar. 31, 2017, provisional application No. 62/416,333, filed on Nov. 2, 2016.

(52) U.S. Cl.
CPC ..... *A61M 2016/0036* (2013.01); *A61M 16/16* (2013.01); *A61M 16/161* (2014.02); *A61M 2205/3365* (2013.01); *A61M 2230/50* (2013.01); *A61M 2230/63* (2013.01)

(56) References Cited

U.S. PATENT DOCUMENTS

| | | | | |
|---|---|---|---|---|
| 5,904,141 | A | 5/1999 | Estes et al. | |
| 6,123,072 | A | 9/2000 | Downs | |
| 6,401,713 | B1 | 6/2002 | Hill et al. | |
| 6,467,477 | B1 | 10/2002 | Frank et al. | |
| 8,573,205 | B2 | 11/2013 | Habashi | |
| 8,752,549 | B2 | 6/2014 | Doyle | |
| 10,213,566 | B2 | 2/2019 | Cortez, Jr. et al. | |
| 11,478,595 | B2 | 10/2022 | Rapoport et al. | |
| 2005/0166922 | A1 * | 8/2005 | Knepper | A61M 16/024 128/204.23 |
| 2006/0249149 | A1 | 11/2006 | Meier et al. | |
| 2008/0097234 | A1 | 4/2008 | Nicolazzi et al. | |
| 2010/0095959 | A1 | 4/2010 | Farrell | |
| 2010/0108066 | A1 | 5/2010 | Martin et al. | |
| 2011/0253136 | A1 * | 10/2011 | Sweeney | A61M 16/024 128/207.18 |
| 2016/0089509 | A1 | 3/2016 | Hete et al. | |
| 2018/0001042 | A1 | 1/2018 | Albanese et al. | |

OTHER PUBLICATIONS

Douglas N. Homnick, "Mechanical Insufflation-Exsufflation for Airway Mucus Clearance," Respiratory Care, vol. 52, Issue 10, Oct. 1, 2007, in 12 pages.

* cited by examiner

METHOD OF DRIVING A FORM OF RESPIRATORY THERAPY

INCORPORATION BY REFERENCE TO PRIORITY APPLICATIONS

Any and all applications for which a foreign or domestic priority claim is identified in the Application Data Sheet as filed with the present application are hereby incorporated by reference under 37 CFR 1.57.

FIELD

The present disclosure relates to respiratory therapy devices and methods for providing ventilatory assistance/respiratory therapy to a user. Such devices and methods can be used, for example, for treating sleep-disordered breathing (SDB), and in particular, to delivering a respiratory therapy or ventilatory assistance to a user of a respiratory therapy device to treat the SDB.

BACKGROUND

Breathing has as one of its core purposes to eliminate $CO_2$. There is a direct relationship between the amount of $CO_2$ eliminated and the total volume of gas moved into and out of the lung (ventilation). In natural (spontaneous) breathing patterns, ventilation is accomplished by moving discrete volumes (tidal volume) in and out at a relatively constant frequency, returning to the same baseline volume (Functional Residual Capacity or FRC) between breaths. Most forms of ventilatory assistance/respiratory therapy use artificial ventilation to attempt to modify the total ventilation by increasing individual tidal volumes, or by forcing extra breaths (each similar to naturally occurring tidal volumes) through increasing respiratory frequency, or by some combination of the two approaches.

Examples of conventional breathing modes used in artificial ventilation include:

1. Total controlled ventilation—the respiratory therapy device delivers a set number of fixed volume or pressure cycles that determine total ventilation without regard for patient efforts. This is often used on paralyzed or deeply sedated patients, but is generally uncomfortable in conscious patients.
2. Intermittent mandatory ventilation (IMV)—the respiratory therapy device delivers fixed numbers of volume or pressure cycles that cause a minimum number of controlled or augmented breaths, mixed in with spontaneous breaths initiated by the patient. However, between each breath (including the mandatory breaths) the patient is allowed to return to FRC.
3. Backup ventilation or rate—the respiratory therapy device switches to total controlled ventilation when the patient experiences either a respiratory pause of a pre-set duration, or when the total average ventilation falls below a pre-set level. At other times, the patient is allowed to breathe at will.
4. Assisted ventilation—the respiratory therapy device, on a patient triggered breath, delivers a set amount of additional volume (sometimes called triggered or synchronized volume ventilation), pressure (sometimes called pressure support ventilation) or some combination of the two.

It has also previously been proposed to provide non-breath based assisted ventilation. This has been proposed to include two modes with very high frequency of very small breaths:

1. High Frequency Jet Oscillation—the ventilator delivers ~250-350 small pulses of pressure jets that result in ~40 cc air movement. Since this is less than the tracheal dead space, the contribution to breathing is by convection and mixing. The jets are typically given directly into the trachea or upper airway of the patient and may cause sufficient CO2 clearance to drop spontaneous breathing to low or zero rate.
2. High Frequency Oscillation—the ventilator delivers small (100 cc) breaths at a somewhat elevated rate (~100/min), providing a low level of overall ventilation.

Both the above modes uses a mechanical ventilation rate well above normal breathing frequencies. They are often combined with Positive End Expiratory Pressure (to elevate the FRC) and prevent atelectasis, but this is not used cyclically for ventilation.

A user's respiratory system responds sensitively to blood $CO_2$ levels and, to a lesser extent, the blood $O_2$ saturation levels. $CO_2$ is a "waste" product of the metabolic consumption of energy stores in the user's body, "burned" in the presence of the oxygen, and producing $H_2O$ in addition to $CO_2$, the latter being transported in the blood to the lung for flushing. The rate at which energy is consumed by the body (the metabolic rate) determines the rate of $O_2$ consumption as well as the $CO_2$ production. The exchange of $O_2$ and $CO_2$ takes place in the lung alveoli and relies on a steady tidal influx of ambient concentrations to match the metabolic rate.

It is well known the metabolic rate is dependent on the level of activity not only when the user is awake, but also during the phases of sleep. The body is highly sensitive to any build-up of blood $CO_2$ with an excess giving rise to metabolic acidosis. The user's breathing rate thus responds strongly to the need for maintaining a normal range of pH level, by flushing excess blood $CO_2$ from the user's system from the lung. The respiratory cycle involves a period of inspiration in which ambient air concentrations effect a dilution of the alveoli $CO_2$ and corresponding to the blood levels of $CO_2$ and expiration which entails the flushing of the lung volume with a characteristically raised level of $CO_2$. The exchange of $CO_2$ at the blood/tissue interface of the alveoli is dependent on the existence of a differential pressure gradient that results from a $CO_2$ concentration around 5% and the ambient CO2 concentration of around 0.4%.

Disordered breathing during sleep can result from changes in physiological, physical or neurological conditions of the user. One example can be an upper airway collapsing from loss of muscle tone, causing obstruction of the upper airway and resulting in relatively rapid build-up of $CO_2$ in the user's lungs and blood system. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression and anxiety. In serious cases, repetitive arousal events can result in sleep deprivation and, over time, an increased risk of further complications and mortality rates. Another example of SDB is Cheyne-Stokes respiration, which is characterized by abnormal periodic pattern of breathing, where one can experience gradual hyperpnea, gradual hypopnea and apnea sequentially.

Conventionally, apneas and hypopneas can be treated by applying sufficient pressure from a pressure-generating device to the user by way of a mask or other types of user interface to restore the upper airway air flow. Treatments can typically involve continuous positive airway pressure (CPAP) and/or bi-level positive airway pressure (bi-level) machines. These machines can process a respiration signal to extract breath features, such as individual phases of inspiration and expiration.

SUMMARY

As described above, the conventional treatments are responsive directly to the breathing cycle of the user and attempt to supplement the natural cycle based on the observed respiration signals, including breathing patterns. While it is possible to directly measure the users' $CO_2$ levels using $CO_2$ sensors, $CO_2$ sensors are not commonly part of the CPAP or bi-level machines. As patients use the CPAP or bi-level machines while they are asleep, additional sensors can be uncomfortable or disrupt the patients' sleep. Additional sensors can also add to the cost of making the CPAP or bi-level machines. Therefore, it would be advantageous to be able to estimate the patient's $CO_2$ levels using hardware already present in the CPAP or bi-level machines. For example, flow sensors and pressure sensors can be among the standard sensors in most CPAP or bi-level machines. The present disclosure differs from conventional methods of analyzing the user's breath features by inputting an observed respiration signal (for example, flow rate or pressure) as a direct, un-interpreted input into a simulation model of the user's metabolic system. For example, the model can simulate the $CO_2$ flushing volume of the user's lung and associated processes. Accordingly, an objective of the present disclosure is to provide a method of driving a respiratory therapy device (for example, a CPAP device) to treat sleep-disordered breathing. The sleep-disordered breathing can include, by way of example and not limitation, obstructive sleep apnea, Cheyne-Stokes respiration, or other disorders, by estimating a user's blood or lung $CO_2$ percentage composition from a dynamic simulation model driven directly by an observed respiration signal measured in the CPAP device.

The estimated blood or lung $CO_2$ level can be used to predict breathing events, such as hypopnea, apnea, and the like, which can be preceded by and/or result in an increase or a decrease in the blood or lung $CO_2$ level. Timely flushing of $CO_2$ from the user's body can mitigate triggers for the breathing events and induce a smoother breathing pattern for the user. The present disclosure advantageously provides an indication of when to flush excess $CO_2$ from the user. Accordingly, another objective of the present disclosure is to provide additional and/or different therapeutic treatments to attempt to reduce the blood or lung $CO_2$ level and prevent the onset of breathing events. For example and not by way of limitation, providing additional and/or different therapeutic treatments can include altering an operating pressure of the respiratory device or providing a different type of therapy such as CPAP, high flow therapy, etc.

Instead of adjusting or increasing the operating pressure of the respiratory therapy device as currently done when an apnea or hypopnea is detected, the pressure provided to the user can be slowly increased over a number of breaths to increase a volume of the user's lungs useful for $CO_2$ flushing and can be quickly reduced during expiration, according to the estimated blood $CO_2$ level and/or the predicted breathing events (hereinafter referred to as "ramp cycle therapy pressure"). In some embodiments, a flow generator of the respiratory therapy device can provide the ramp cycle therapy pressure cyclically at predetermined rates. For example and not by way of limitation, the ramp cycle therapy pressure can have a waveform of a ramp wave. The ramp cycle therapy pressure can augment the flushing of $CO_2$ from the user's body, which can mitigate triggers for the predicted breathing events. Accordingly, yet another aspect of the present disclosure is to provide a ramp cycle therapy to treat sleep-disordered breathing.

According to some embodiments, a method of estimating $CO_2$ levels from a user's respiration signal can include obtaining the respiration signal and estimating a current $CO_2$ level of the user by modeling the user's respiratory system based on the respiration signal.

In some embodiments, the method of estimating $CO_2$ levels from a user's respiration signal can further include predicting a breathing event based on the estimated $CO_2$ levels. In some embodiments, the method of estimating $CO_2$ levels from a user's respiration signal can further include responding to increased estimated $CO_2$ levels. In some embodiments, the responding to the increased estimated $CO_2$ levels can include increasing a pressure of a respiratory therapy to the user. In some embodiments, the increasing of the pressure can be for a predetermined period of time. In some embodiments, the respiration signal can be flow rate, pressure data, or thoracic movement of the user. In some embodiments, the current $CO_2$ level of the user can include a lung $CO_2$ level of the user. In some embodiments, the current $CO_2$ level of the user can include a blood $CO_2$ level of the user.

According to some embodiments, a respiratory therapy device can include one or more sensors configured to measure a respiration signal of a user and a controller configured to estimate a current $CO_2$ level of the user by modeling the user's respiratory system based on the respiration signal. In some embodiments, the controller of the respiratory therapy device can be further configured to predict a breathing event based on estimated $CO_2$ level of the user. In some embodiments, the controller of the respiratory therapy device can be further configured to respond to increased estimated $CO_2$ levels of the user. In some embodiments, the controller of the respiratory therapy device can be further configured to respond to the increased estimated $CO_2$ levels by increasing a therapeutic pressure to the user. In some embodiments, the controller of the respiratory therapy device can be further configured to increase the therapeutic pressure to the user for a predetermined period of time. In some embodiments, the current $CO_2$ level of the user comprises a blood $CO_2$ level of the user.

According to some embodiments, a ramp cycle therapy can include detecting an indication of a rise in $CO_2$ levels of a user, increasing a pressure supplied to the user from a therapy pressure to a first pressure over a predetermined number of breaths in response to the indication of the rise in $CO_2$ levels of the user, and after the first pressure is reached, decreasing the pressure supplied to the user from the first pressure to the therapeutic pressure during exhalation.

In some embodiments, the detecting the indication of the rise in the $CO_2$ levels in the ramp cycle therapy can further include measuring a respiration signal, and estimating a current $CO_2$ level of the user by modeling the user's respiratory system based on the respiration signal. In some embodiments, the increasing of the pressure supplied to the user from the therapy pressure to the first pressure in the ramp cycle therapy can further include increasing the pressure by about 4-6 cm $H_2O$. In some embodiments, the predetermined number of breaths in the ramp cycle therapy can be adjusted based on the current $CO_2$ level. In some embodiments, the increasing of the pressure supplied to the user from the therapy pressure to the first pressure in the ramp cycle therapy can include increasing a $CO_2$ flushing volume of the user's lungs. In some embodiments, the $CO_2$ flushing volume of the user's lungs in the ramp cycle therapy can increase by about 100 mL/cm $H_2O$. In some embodiments, the current $CO_2$ level of the user in the ramp cycle therapy can comprise a blood or lung $CO_2$ level of the user. The respiration signal may be flow rate, pressure data, or thoracic movement of the user.

According to some embodiments, a respiratory therapy device can include a gases source supplying a flow of gases, a conduit providing the flow of gases to a user, and a controller configured to control a pressure of the gases supplied to the user. The controller can be configured to detect an indication of a rise in $CO_2$ levels of the user. The controller can be further configured to, in response to the indication of the rise in $CO_2$ levels of the user, increase the pressure of the gases supplied to the user from a therapy pressure to a first pressure over a predetermined number of breaths, and after the first pressure is reached, to decrease the pressure of the gases supplied to the user from the first pressure to the therapeutic pressure during exhalation. In some embodiments, the respiratory therapy device can further comprise one or more sensors configured to measure a respiration signal of a user, wherein the controller is configured to detect the indication of the rise in the $CO_2$ levels by estimating a current $CO_2$ level of the user by modeling the user's respiratory system based on the respiration signal. In some embodiments, the controller of the respiratory therapy device can be further configured to increase the pressure supplied to the user from the therapy pressure to the first pressure by increasing the pressure by about 4-6 cm $H_2O$. In some embodiments, the controller of the respiratory therapy device can be further configured to adjust the predetermined number of breaths based on the current $CO_2$ level. In some embodiments, the controller of the respiratory therapy device can be further configured to increase the pressure supplied to the user by increasing a $CO_2$ flushing volume of the user's lungs. In some embodiments, the controller of the respiratory therapy device can be further configured to increase the $CO_2$ flushing volume of the user's lungs by about 100 mL/cm $H_2O$. In some embodiments, the current $CO_2$ level of the user comprises a blood $CO_2$ level of the user. In some embodiments, the current $CO_2$ level of the user comprises a lung $CO_2$ level of the user. In some embodiments, the respiration signal can be flow rate, pressure data, or thoracic movement of the user.

According to some embodiments a respiratory therapy device is configured to supply a flow of breathable gas to a user via a breathing gas delivery conduit and a patient interface; the device comprising:

a controller configured to control a pressure of the gas supplied to the user; and one or more sensors configured to measure data relating to a patient's breathing pattern;

wherein the controller is configured to control the device according to a variable ventilation profile to increase the pressure of the breathable gas supplied to the user from a first pressure to a second pressure over more than one breath;

the controller being further configured, after the second pressure is reached or maintained for a predetermined period of time, to:

decrease the pressure of the gas supplied to the user from the second pressure to the first pressure during one or more periods of exhalation; and/or maintain the pressure of the gas supplied to the user at the second pressure during a period of exhalation.

The controller may be configured to increase the pressure of the breathable gas supplied to the user from the first pressure to the second pressure over a predetermined number of breaths.

The increased pressure may be supplied asynchronously, semi-synchronously or synchronously with all or part of the breathing pattern of the user. The pressure of the gas supplied to the user may be decreased during a single period of exhalation. The controller may be configured to control the device to increase the pressure of the breathable gas supplied to the user from the first pressure to the second pressure via a single step increase from the first pressure to the second pressure. The controller may be configured to control the device to increase the pressure of the breathable gas supplied to the user from the first pressure to the second pressure via a plurality of step increases from the first pressure to the second pressure. The controller may be configured to control the device to increase the pressure of the breathable gas supplied to the user from the first pressure to the second pressure via at least one ramped increase from the first pressure to the second pressure. The controller may be configured to control the device to increase the pressure of the breathable gas supplied to the user from the first pressure to a second pressure via a plurality of ramped increases from the first pressure to the second pressure.

The first and/or second pressure may remain constant or increase over successive cycles.

The one or more sensors may be configured to measure at least one respiration signal of a user, wherein the respiration signal may be indicative of any one of the following:

the onset, duration and/or end of inspiration; the onset, duration and/or end of expiration; a rise in the $CO_2$ levels by estimating a current $CO_2$ level of the user by modeling the user's respiratory system based on the respiration signal. The respiration signal may be indicative of any one or more of flow rate, pressure data, or thoracic movement of the user.

The controller may be configured to increase the pressure supplied to the user from the first pressure to the second pressure by increasing the pressure by about 1 to 15 cm $H_2O$, preferably by about 2 to 10 cm $H_2O$, and more preferably 4 to 6 cm $H_2O$.

The controller may be configured to adjust the predetermined number of breaths over which the increased pressure is supplied in response to a characteristic of the user's breathing pattern. The characteristic may be the current $CO_2$ level.

The controller may be configured to supply a flow of breathable gas to a patient where the pressure of the gas is based on two or more therapy profiles that the controller is controlling the device to provide simultaneously; wherein the second therapy profile is different from the first therapy profile, the controller being configured to superimpose the two therapy profiles.

In some embodiments the variable ventilation profile is not the ventilation profile of FIGS. 5A and 5B.

According to some embodiments a respiratory therapy device is configured to supply a flow of breathable gas to a user via a breathing gas delivery conduit and a patient interface; the device comprising:

a controller configured to control the flow of gas supplied to the user; and

- at least one sensor configured to measure data relating to a patient's breathing pattern;
- wherein the controller is configured according to a ramp cycle in which the pressure of the gases supplied to the user is increased between first and second threshold pressures over a predetermined number of breaths, and after the second threshold is reached, to rapidly decrease the pressure of the gases supplied to the user to the first threshold pressure during an exhalation phase of one breath.

The ramp cycle may have a saw tooth profile, gradually ramping upwards and then dropping sharply during the exhalation phase.

The pressure increase from the first to second threshold pressures may be:

- over a predetermined number of breaths taken by the user.
- any one of, or a combination of, a linear, exponential or stepped increase.

The thresholds may be dependent upon a therapeutic pressure set by the user. The therapeutic pressure may be in the range of 4 to 20 cm $H_2$. The therapeutic pressure may change throughout the therapy, in response to breathing events such as apneas and the like.

According to some embodiments a respiratory therapy device is configured to supply a flow of breathable gas to a user via a breathing gas delivery conduit and a patient interface; the device comprising:

- a controller configured to control a property of the gas supplied to the user; and
- at least one sensor configured to measure data relating to a patient's breathing pattern;
- wherein the controller is configured to increase a property of the gas supplied to the user from a first threshold to a second threshold over more than one breath; wherein
- all or part of the increase is supplied over more than one breath and is supplied asynchronously, semi-synchronously and/or synchronously, with the breathing pattern of the user;
- the controller being further configured after the second threshold is reached, or maintained for a predetermined period of time, to decrease the property of the gas supplied to the user from the second threshold during one or more periods of exhalation.

According to some embodiments a respiratory therapy device is configured to supply a flow of breathable gas to a user via a breathing gas delivery conduit and a patient interface; the device comprising:

- a controller configured to control a property of the gas supplied to the user; and
- at least one sensor configured to measure data relating to a patient's breathing;
- wherein the controller is configured to supply a flow of breathable gas to a patient where the pressure of the gas is based on two or more therapy profiles that the controller is controlling the device to provide simultaneously; wherein
- the second therapy profile is different from the first therapy profile, and the controller is configured to superimpose the two therapy profiles.

The first therapy profile may comprise supplying an increased pressure of the gases supplied to the user from a first pressure to a second pressure over at least one breath, the increased pressure being supplied asynchronously with the breathing pattern of the user and after the second pressure is reached or maintained for a predetermined time period, decreasing the pressure of the gas supplied to the user from the first pressure to the therapeutic pressure during one or more periods of exhalation.

The second therapy profile may be selected from any one or more of the following profiles:

a) Continuous Positive Airway Pressure (CPAP);
b) Nasal High Flow (NHF);
c) Bi-level;
d) Non-Invasive Ventilation (NIV).

According to some embodiments a method of providing respiratory therapy using a device configured to supply a flow of breathable gas to a user via a breathing gas delivery conduit and a patient interface; comprises steps of:

using a controller of the device to control the device according to a variable ventilation profile to:

a) increase the pressure of the breathable gas supplied to the user from a first pressure to a second pressure over more than one breath;
b) after the second pressure is reached or maintained for a predetermined period of time, to:
c) decrease the pressure of the gas supplied to the user from the second pressure to the first pressure during one or more periods of exhalation; and/or
d) maintain the pressure of the gas supplied to the user at the second pressure during a period of exhalation The method may comprise increasing the pressure of the breathable gas supplied to the user from the first pressure to the second pressure over a predetermined number of breaths.

The increased pressure may be supplied asynchronously, semi-synchronously or synchronously, with the breathing pattern of the user, that is, in respect of the timing of the increased pressure with the inspiratory and/or expiratory phases of the breath.

The pressure of the gas supplied to the user may be decreased during a single period of exhalation. The pressure of the breathable gas supplied to the user may be increased from the first pressure to the second pressure via a single step increase from the first pressure to the second pressure. The pressure of the breathable gas supplied to the user from the first pressure to the second pressure may be increased via a plurality of step increases from the first pressure to the second pressure. The pressure of the breathable gas supplied to the user from the first pressure to the second pressure may be increased via at least one ramped increase from the first pressure to the second pressure. The pressure of the breathable gas supplied to the user from the first pressure to a second pressure may be increased via a plurality of ramped increases from the first pressure to the second pressure.

The first and/or second pressure may increase or remain constant over successive cycles.

The pressure supplied to the user may be increased from the first pressure to the second pressure by about 1 to 15 cm $H_2O$, preferably by about 2 to 10 cm $H_2O$, and more preferably 4 to 6 cm $H_2O$.

The predetermined number of breaths over which the increased pressure is supplied may be adjusted in response to a characteristic of the user's breathing pattern, such as current $CO_2$ level for example.

The pressure of the gas supplied to the patient may be based on two or more therapy profiles that the controller is controlling the device to provide simultaneously; wherein the second therapy profile is different from the first therapy profile, and the controller is configured to superimpose the two therapy profiles.

In some examples the variable ventilation profile is not the ventilation profile of FIGS. 5A and 5B.

According to some embodiments a method of providing respiratory therapy using a device configured to supply a flow of breathable gas to a user via a breathing gas delivery conduit and a patient interface; comprises steps of:

using a controller of the device to control the device to:

provide a ramp cycle in which the pressure of the gases supplied to the user is increased between first and second threshold pressures over a predetermined number of breaths, and after the second threshold is reached, to rapidly decrease the pressure of the gases supplied to the user to the first threshold pressure during an exhalation phase of one breath.

The ramp cycle may have a saw tooth profile, gradually ramping upwards and then dropping sharply during the exhalation phase.

According to some embodiments a method of providing respiratory therapy using a device configured to supply a flow of breathable gas to a user via a breathing gas delivery conduit and a patient interface; comprises steps of:

using a controller of the device to control the device to:

increase a property of the gas supplied to the user from a first threshold to a second threshold over more than one breath; wherein all or part of the increase is supplied over more than one breath and is supplied asynchronously, semi-synchronously and/or synchronously with the breathing of the user; and after the second threshold is reached, or maintained for a predetermined period of time, decrease the property of the gas supplied to the user from the second threshold during one or more periods of exhalation.

According to some embodiments a method of providing respiratory therapy using a device configured to supply a flow of breathable gas to a user via a breathing gas delivery conduit and a patient interface; comprises steps of:

using a controller of the device to control the device to:

supply a flow of breathable gas to a patient where the pressure of the gas is based on two or more therapy profiles that the controller is controlling the device to provide simultaneously; wherein the second therapy profile is different from the first therapy profile, and the controller is configured to superimpose the two therapy profiles.

The first therapy profile may comprise supplying an increased pressure of the gases supplied to the user from a first pressure to a second pressure over at least one breath, the increased pressure being supplied asynchronously with the breathing pattern of the user and after the second pressure is reached or maintained for a predetermined time period, decreasing the pressure of the gas supplied to the user from the first pressure to the therapeutic pressure during one or more periods of exhalation.

According to some embodiments a respiratory therapy device configured to supply a flow of breathable gas to a user via a breathing gas delivery conduit and a patient interface; comprises:

a controller configured to control the gas flow supplied to the user; and one or more sensors configured to measure data relating to a patient's breathing pattern;

wherein the controller is configured to control the device according to a variable ventilation profile to increase the pressure of the breathable gas supplied to the user from a first pressure to a second pressure over a first period lasting more than one breath;

the controller being further configured, after the second pressure is reached or maintained for a predetermined period of time, to decrease the pressure of the gas supplied to the user from the first pressure to the therapeutic pressure over a period of time that is less than the first period.

The respiratory therapy device as above may further comprise any one or more of:

a flow generator;

a patient interface;

an expiratory conduit;

one or more connectors configured to connect one component of the device to another;

a humidifier configured to humidify the flow of gas to the patient.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 6(*b*) illustrates an exemplary user's respiration signal in dashed line, with the solid line indicating the ventilatory assistance provided by another prior art respiratory therapy system.

FIG. 7(*b*) illustrates the total ventilation of an exemplary user, being the sum of the exemplary user's respiration signal and the ventilatory assistance of FIG. 7A.

FIG. 8(*b*) illustrates the total ventilation of an exemplary user, being the sum of the exemplary user's respiration signal and the ventilatory assistance of FIG. 8A.

FIG. 9(*b*) illustrates the total ventilation of an exemplary user, being the sum of the exemplary user's respiration signal and the ventilatory assistance of FIG. 9A.

DETAILED DESCRIPTION OF THE PREFERRED EMBODIMENT

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
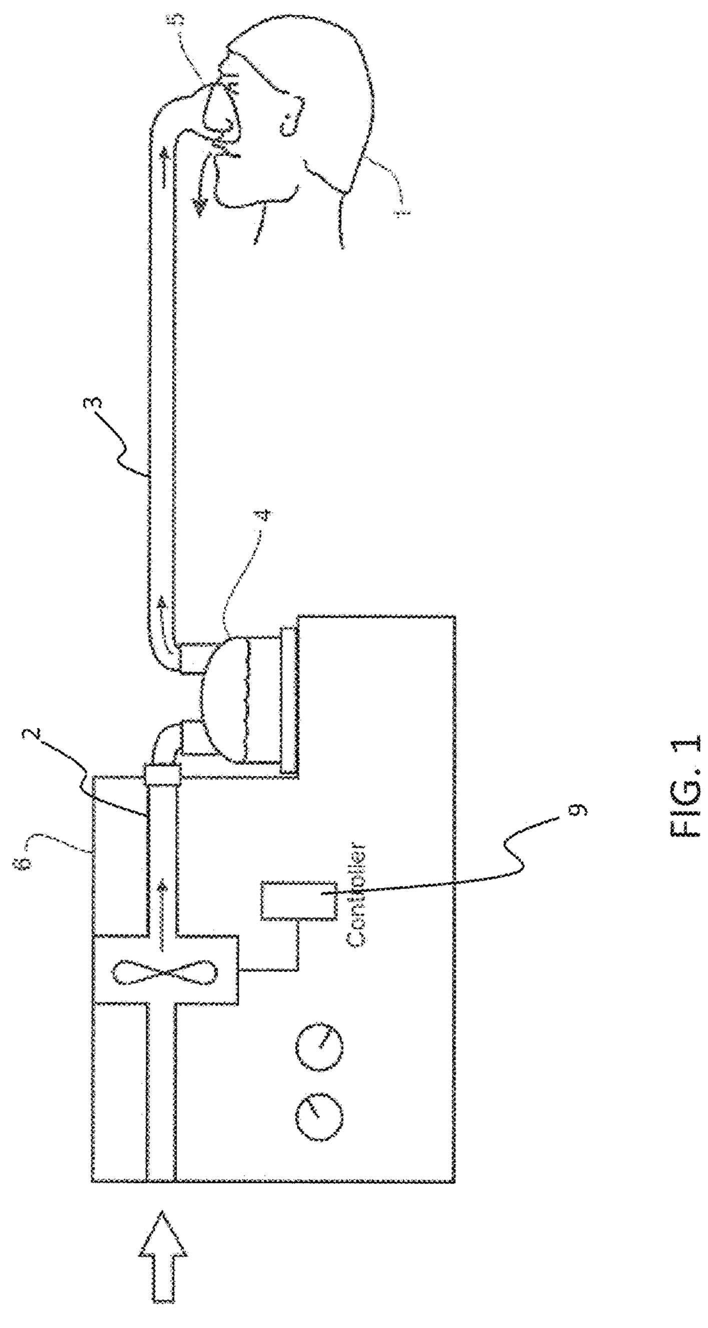
FIG. 1 illustrates a schematic representation of an embodiment of a respiratory therapy device.

A schematic representation of a respiratory therapy device is provided in FIG. 1. The respiratory therapy device can comprise, or be configured to be connected to, a breathable gas source such as a blower unit 6 in fluid communication with a humidifier 4 via a conduit 2. In other examples, the gas source may comprise a stored source of pressurized gas to which the device can be connected. An inspiratory or breathable gas delivery tube 3 can provide a flow of gases generated by the blower unit 6 and humidified by the humidifier 4 to a user 1 via a patient interface 5. The patient interface 5 can be a full face mask that can provide a flow of gases to the user's airways via the user's mouth and nose. The patient interface 5 can also be an oral interface or a nasal interface, or a tracheal interface. The nasal interface may comprise one or more nasal prongs. In some examples, the nasal prongs comprise nasal cushions or pillows configured to seal against the nares of the user. In nasal high flow (NHF) therapy, the prongs are configured not to seal against the patient's nares such that there is a leak flow path around the prongs. In some embodiments, the humidifier can be optional in the respiratory therapy device. General operation of the respiratory therapy device will be known to those skilled in the art and will not be described here in detail. In some embodiments, one or more controllers 7 can control the blower unit 6 to generate a gas flow of a desired flow rate and/or pressure. The gas flow can be directed through the conduit 2 to the humidifier 4 to be humidified. The humidified gas can be directed through the inspiratory tube 3 and the patient interface 5 to the user 1. The controller 9 can be programmed with or can determine a suitable flow rate and/or pressure. Sensors (not shown) can be placed in various locations in the respiratory therapy device. For example and not by way of limitation, the sensors can include any one or more of: flow, pressure, temperature, and/or humidity sensors. Output(s) from the sensors can be received by the controller 9 to assist the controller 9 to operate the respiratory therapy device in a manner that can provide the desired therapy. By 'respiratory therapy device' we include any device configured to supply breathable gas to a patient or user, and we include a ventilator as might be used in a hospital to supply all of the required volume of breathing gas to a patient, and any other type of device configured to supply any proportion of the required volume of breathing gas to a user.

Respiratory System and Metabolic Rate Model

An aspect of the present disclosure is to provide a method of driving a respiratory therapy device to treat sleep-disordered breathing by estimating a user's blood or lung $CO_2$ percentage composition from a dynamic lung model driven directly by an observed respiration signal measured in the respiratory therapy device. In some embodiments, the method can simulate the user's pulmonary system by taking a respiration signal, estimating a gas exchange rate, and determining a ratio of gases in the lungs for any given time. For example and not by way of limitation, the respiratory therapy device can be a CPAP machine. For example and not by way of limitation, the observed respiration signal can be a flow signal. Sleep-disordered breathing can include obstructive sleep apnea, Cheyne-Stokes respiration, etc. The method can comprise an input, which can be a measured parameter, a respiratory system simulator, and an output, which can be an estimated parameter.

Figure 2A:
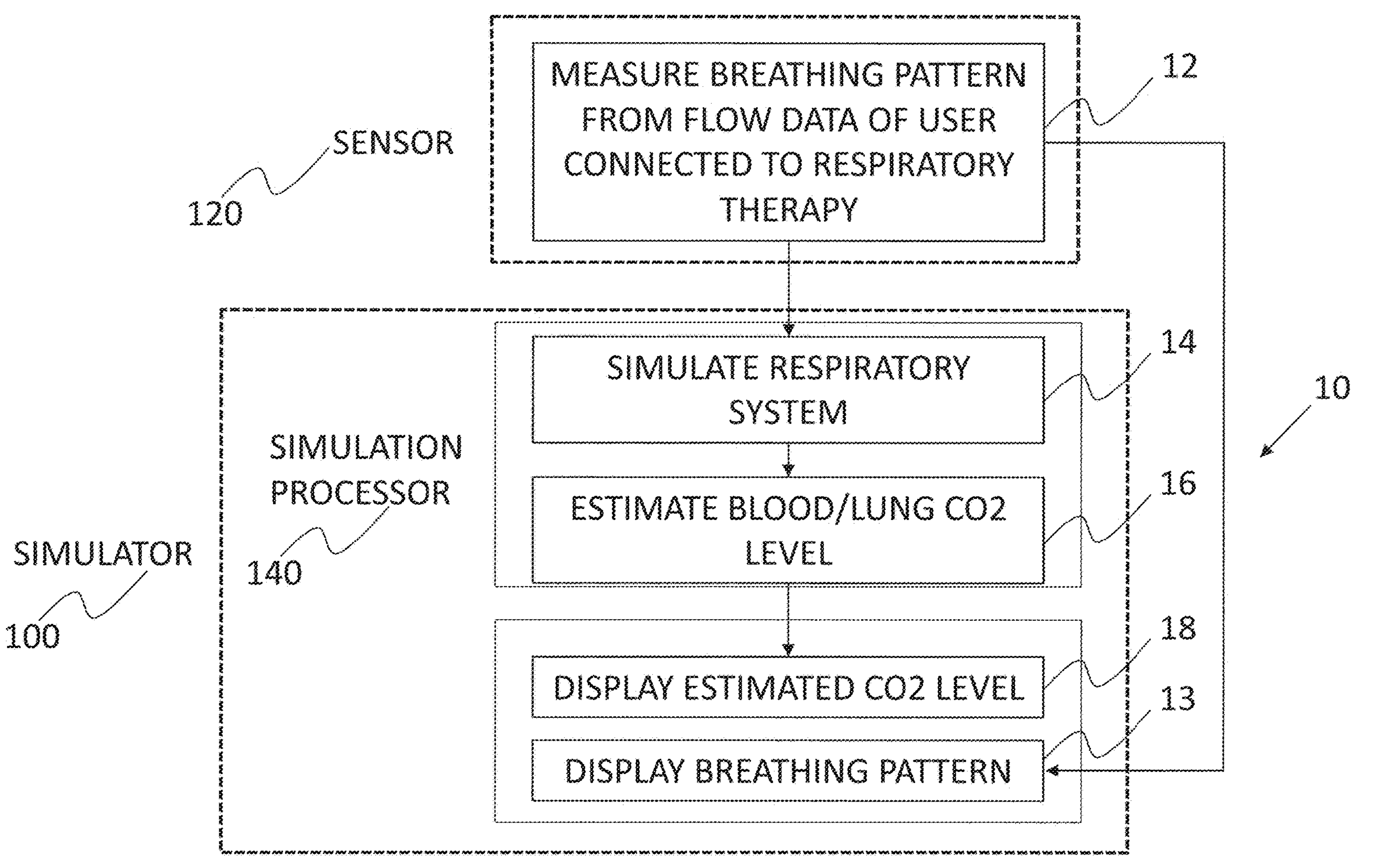
FIG. 2A illustrates a flowchart of an embodiment of a method of estimating $CO_2$ levels from a user's respiration signal.

As shown in FIG. 2A, the input can be a respiration signal of a user connected to a CPAP machine or other medical device in a method 10 of estimating the user's $CO_2$ levels. The respiration signal can be detected and measured 12 by one or more sensors 120. The sensors 120 can be built into the CPAP machine or the other medical device connected to the user, or stand-alone sensors. In some embodiments, the sensors 120 can be located in the inspiratory (and/or expiratory tubes, if present) of the CPAP machine. The respiration signal can be quantified by a measured flow rate of the CPAP device. In other embodiments, the respiration signal can be quantified by the user's airway pressure. In some embodiments, the input can be from a flow sensor in the respiratory device, determining a flow in the device. For example and not by way of limitation, the flow can be determined from a motor speed and/or a pressure within a flow path. In some embodiments, the input can be from a sensor attached to a thorax of the user, such as by inductance plethysmography. The sensor can estimate the flow by determining displacement of the user's chest, or by any known means of determining the flow. In some embodiments, the measured respiration signal can optionally be displayed 13. For example and not by way of limitation, the measured respiration signal can be displayed 13 graphically.

With continued reference to FIG. 2A, the respiration signal, such as the flow rate, can be used by the respiratory dynamics simulator device 100 to simulate 14 the user's metabolic system. The respiratory dynamics simulator device 100 can be built into the CPAP machine or other medical device connected to the user, or a stand-alone hardware processor. The respiration signal can be input into a simulation processor 140 of the respiratory dynamics simulator device 100. The simulation processor 140 can be configured to simulate the user's metabolic system by utilizing at least one of the following parameters or combinations thereof: a total lung volume, a functional residual capacity of the lung, a tidal lung volume, a rate of infusion of $O_2$ out of total lung volume, a rate of infusion of $CO_2$ into total lung volume, a N2 content value, and a blood or lung $CO_2$ percentage. One of ordinary skill in the art will appreciate from the disclosure herein that other suitable parameters can be included instead of or in addition to any of the above-referenced parameters. Details of those parameters are described below.

Tidal Lung Volume V. The tidal lung volume can be a volume of air that is inhaled or exhaled in a single breath over and above the Functional Residual Capacity (discussed below). This volume is dependent on a state of the breath (inspiration, expiration).

Functional Residual Capacity FRC, The functional residual capacity can be the volume of gas in the lungs at a resting expiratory level, that is, the volume of air present in the lungs at the end of passive expiration. The functional residual capacity of users can be about 2-4 L. In some embodiments, the simulation processor 140 can use a variable functional residual capacity ranging from about 0 L to about 5 L. The range of the functional residual capacity is not limiting and can be any range. In some embodiments, the user's functional residual capacity can be estimated by characteristics such as height and weight, or the altitude of the user's residence, or could be measured directly, for example, by nitrogen washout or helium dilution.

Total Lung Volume VT=V+FRC, The total lung volume can be a dynamic variable representing the sum of the functional residual capacity and the tidal volume. The total lung volume can be greater or equal to 0 L, that is, VT≥0. In other words, the total lung volume can represent a total volume of fluid in the user's lungs at a given point in time of the respiratory cycle.

Rate of infusion of $CO_2$ into Total Lung Volume. This parameter can be the rate of infusion of $CO_2$ into the instantaneous total lung volume as a result of gas exchange in the alveoli. In some embodiments, the rate of infusion of $CO_2$ into the total lung volume can be an adjustable variable. In some embodiments, the rate of infusion of $CO_2$ into the total lung volume can be set at a rate such that under a normal breathing pattern, the user's blood $CO_2$ level is approximately 5%. This rate can correlate with and reflect the user's metabolic rate.

Rate of infusion of $O_2$ out of Total Lung Volume. This parameter can be the rate of infusion of $O_2$ out of the instantaneous total lung volume as a result of gas exchange in the alveoli. In some embodiments, the rate of infusion of $O_2$ out of the total lung volume can be an adjustable variable. In some embodiments, the rate of infusion of $O_2$ out of the total lung volume can be set at a rate commensurate with an about 4-5% average blood $CO_2$ level. This rate can be dependent at least in part on the user's metabolic rate.

$N_2$ Content Value. In some embodiments, the $N_2$ content value can be a dynamic value based on the total lung volume, the $CO_2$ levels, the $O_2$ levels, and/or a flushing rate of gases present in the lungs. In some embodiments, the $N_2$ content value can also be expressed as a value representing composition of respiratory gases other than $O_2$ and $CO_2$.

Figure 2B:
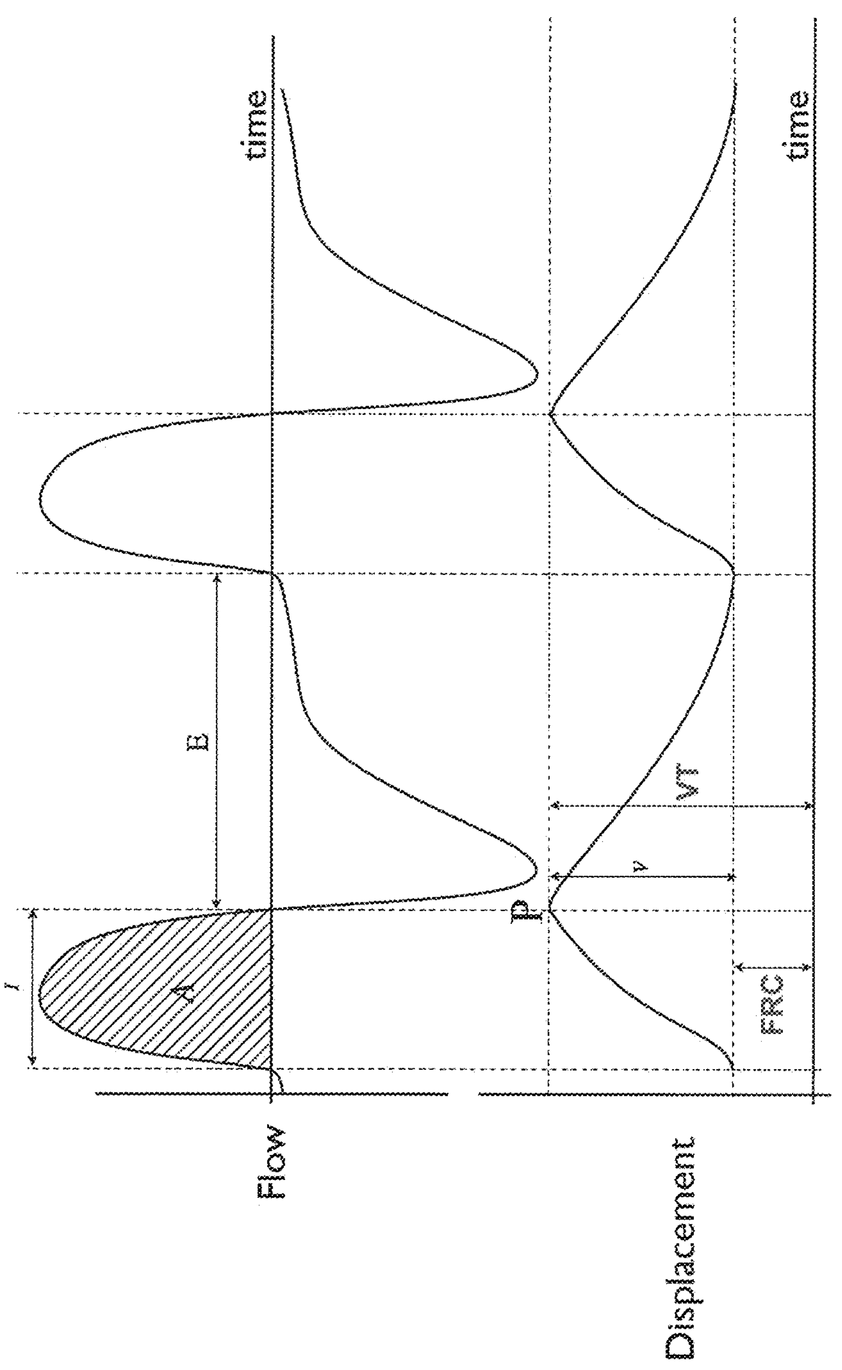
FIG. 2B illustrates exemplary flow rate and lung displacement volume patterns of a user.

Details of an embodiment of the simulation model that can be implemented by the simulation processor 140 will now be described with reference to FIG. 2B. FIG. 2B illustrates exemplary flow rate and lung displacement volume patterns of a user. In some embodiments, air can be inspired at ambient gases concentrations and exhaled at concentration of gases in the lung. Concentrations of the exhaled gases can vary over time depending on various factors including but not limited to a respiration rate and a gas exchange rate. In some embodiments, the ambient air is assumed to be composed of approximately 79.2% nitrogen ($N_2$), 20.4% oxygen ($O_2$), and 0.4% carbon dioxide ($CO_2$). One of ordinary skill in the art would appreciate that these levels of gases could vary. For example and not by way of limitation, the ambient $CO_2$ level may be assumed to be higher than 0.4% as $CO_2$ levels rise in closed rooms due to exhalation by people in the closed rooms. In some embodiments, at the beginning of a therapy session, an assumed lung $CO_2$ composition can be 5%. However, this assumed composition may vary, for example in a non-limiting range between about 4% and about 6%.

As shown in FIG. 2B, a user's respiratory cycles can typically involve an inspiration phase I and an expiration phase E, with a peak of the lung displacement P indicating when the user transits from inspiration to expiration. An area under the flow rate A over an inhalation phase is a volume of air inhaled in that breath (hereinafter referred to as "maximum tidal volume" and corresponding to Vin the lung displacement pattern). While simple integration of the flow rate could be used to determine the volume of gases being inspired and exhaled, the simple integration does not take into account an anatomical dead space (i.e. the upper airways) when analyzing current gases concentrations in the inhaled air. The simple integration also may not take into account the dead space of a breathing circuit of the CPAP or bi-level machine, which can further increase the dead space over and above the dead space of the upper airways. On inhalation, the first gases that reach the lungs are from the dead space of upper airways, which typically has been exhaled from the lungs in a previous breath, and can have deviations from ambient air concentrations. The deviations can be taken into account in the simulation model in some embodiments. In one embodiment, volumes of a mask and/or a breathing tube can also be taken into account as dead spaces in the model.

In some embodiments, the inspiration phase signal can be filtered to take into account the dead space of the upper airways and optionally of the mask and breathing tube. The exponential filter can have a time constant set to effectively model a delay caused by the additional upper airways volume and travelling of the air through the upper airway. The time constant can also take into account the physiology of the upper airways, such as a path length, volume, geometry, and the like. In a non-limiting example, the time constant may be adjusted to more accurately model the delay in air of ambient concentration reaching the lungs by taking into account that the patient has a larger anatomical dead space, or is using a full face mask over a nasal mask.

The filtered inspiration phase signal can be integrated for each of $N_2$, $O_2$, and $CO_2$ to determine a relative tidal volume of each of the three gases in the lungs. When calculating gases concentrations in the lungs, the model may take into account the volume of a functional residual capacity (illustrated as FRC in FIG. 2B), which is the volume of air still remaining in a user's lungs after passive expiration. The total volume in the lungs at an end of the inspiration phase can be a sum of the tidal volume at the end of the inspiration and the functional residual capacity, for example, as shown in FIG. 2B, where VT is the sum of V±FRC.

Because the functional residual capacity can be an assumed parameter, the model can further include a feedback process to adjust an initial total volume to match an observed total volume. In some embodiments, the model can use a nominal functional residual capacity, which is the functional residual capacity and one half of the maximum tidal volume, based on an average over a period of time. In some embodiments, the model may not be critically dependent on the functional residual capacity. Alternatively, the model can use a simple fixed estimate of the functional residual capacity, for example, as shown in FIG. 9B.

At all times a running total of the ratio of the three gases can be tracked. Gas exchange occurs continuously in the lung alveoli. $O_2$ can diffuse out of the lungs and into the bloodstream, and $CO_2$ can diffuse out of the blood stream and into the lungs. Gas exchange occurs regardless of breathing, and changes the concentration of these gases in the lungs. A gas exchange rate within the lungs can vary depending on a metabolic demand of the patient. Diffusion rates of the gases used in the model can be set by calibrating the model. Predetermined breath parameters can be fed into the model for the calibration, and the $O_2$ and $CO_2$ alveoli exchange rates can be adjusted to achieve approximately 5% $CO_2$ level in the lung volume. In some embodiments, the predetermined parameters can include a 500 ml tidal volume at 15 breaths/min. In one embodiment, a ratio of $O_2$ to $CO_2$ exchange rates can be set at 0.8.

In other embodiments, the $CO_2$ and $O_2$ exchange rates may be set at an assumed rate in litres per minute. While an assumed rate is used, the rate could be set by a clinician based on a patient's physical traits, for example age, height, weight, or other physical traits that can affect metabolic rate. The rates could also be measured experimentally in a sleep lab before the patient commences therapy. These assumptions may also change with time, and the model may dynamically change over several nights of therapy as data is gathered.

As described above, the exhalation phase signal can be isolated from the respiration signal. The exhalation phase signal can be integrated to determine a volume of gases being exhaled. The ratio of gases can be changing during exhalation as gas exchange occurs continuously in the lung. The $CO_2$ concentration can rise slightly during exhalation.

By modeling the inspiration and expiration phase signals along with the gas exchange in the lungs, a real-time estimate of the patient's $CO_2$ level can be determined. As previously described, a higher $CO_2$ level can correlate with higher probability of a breathing event. As such, a CPAP or bi-level controller can be configured to respond to the changing $CO_2$ level by increasing the therapeutic pressure above the set pressure, or using a ramp cycle therapy before a breathing event occurs, which will be described in greater detail below. One of ordinary skill in the art would appreciate that other ways of responding to the increased $CO_2$ levels may be possible.

Returning to FIG. 2A, the output of the method can be the user's estimated lung or blood $CO_2$ level in some embodiments. Other indicators of the user's metabolic rate can also be estimated. For example and not by way of limitation, the user's estimated blood $CO_2$ level can be the blood $CO_2$ percentage composition, concentration, or any other suitable indicator of the blood $CO_2$ level. The blood $CO_2$ level can be estimated 16 by the simulation processor 140 using one or more of the above-referenced parameters. The blood $CO_2$ level can correlate with and be an indicator of the user's metabolic rate. The estimated blood $CO_2$ level can be displayed 18 on the display device 180. For example and not by way of limitation, the estimated blood $CO_2$ level can be displayed 13.

Figure 3A:
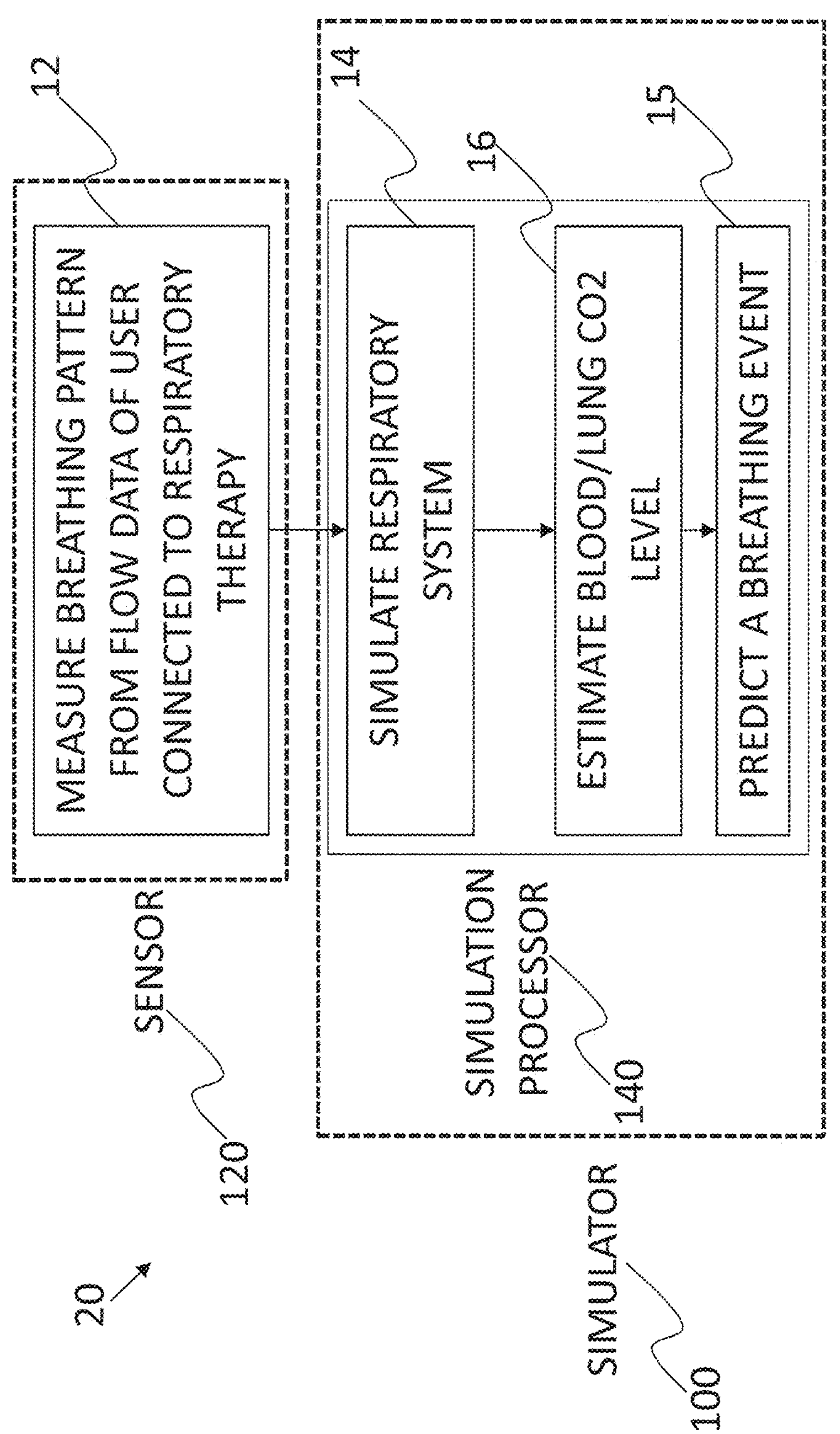
FIG. 3A illustrates a flowchart of an embodiment of a method of estimating $CO_2$ levels from a user's respiration signal.

Turning to FIG. 3A, in addition to features of the method 10 described above, a method 20 of driving a medical device to treat sleep-disordered breathing can further include an additional output. For example and not by way of limitation, the medical device can be a CPAP machine. In some embodiments, the additional output can be a prediction of breathing events. The predicted breathing events can include but are not limited to, hyperpnea, hypopnea, and/or apnea. The simulation processor 140 can use the estimated blood or lung $CO_2$ level to predict 15 occurrences of the breathing events. In some embodiments, the predicted breathing events can be displayed 17 on the display device 180. For example and not by way of limitation, the predicted breathing events can be displayed 17 graphically and/or in text on the display device 180. In some embodiments, the respiratory signal, the estimated blood $CO_2$ level, and/or the breathing events can be displayed concurrently. For example and not by way of limitation, graphs of the respiratory signal, the estimated blood $CO_2$ level, and/or the breathing events can be superposed on each other. The concurrent displays can advantageously show a relationship among the respiratory signal, the estimated blood $CO_2$ level and/or the breathing events. In some embodiments, the respiratory signal, the estimated blood $CO_2$ level, and/or the breathing events can be displayed separately or sequentially. One of ordinary skill in the art would appreciate that a display device may not be required because the user would normally use the respiratory therapy device during sleep and need not see the display.

Figure 3B:
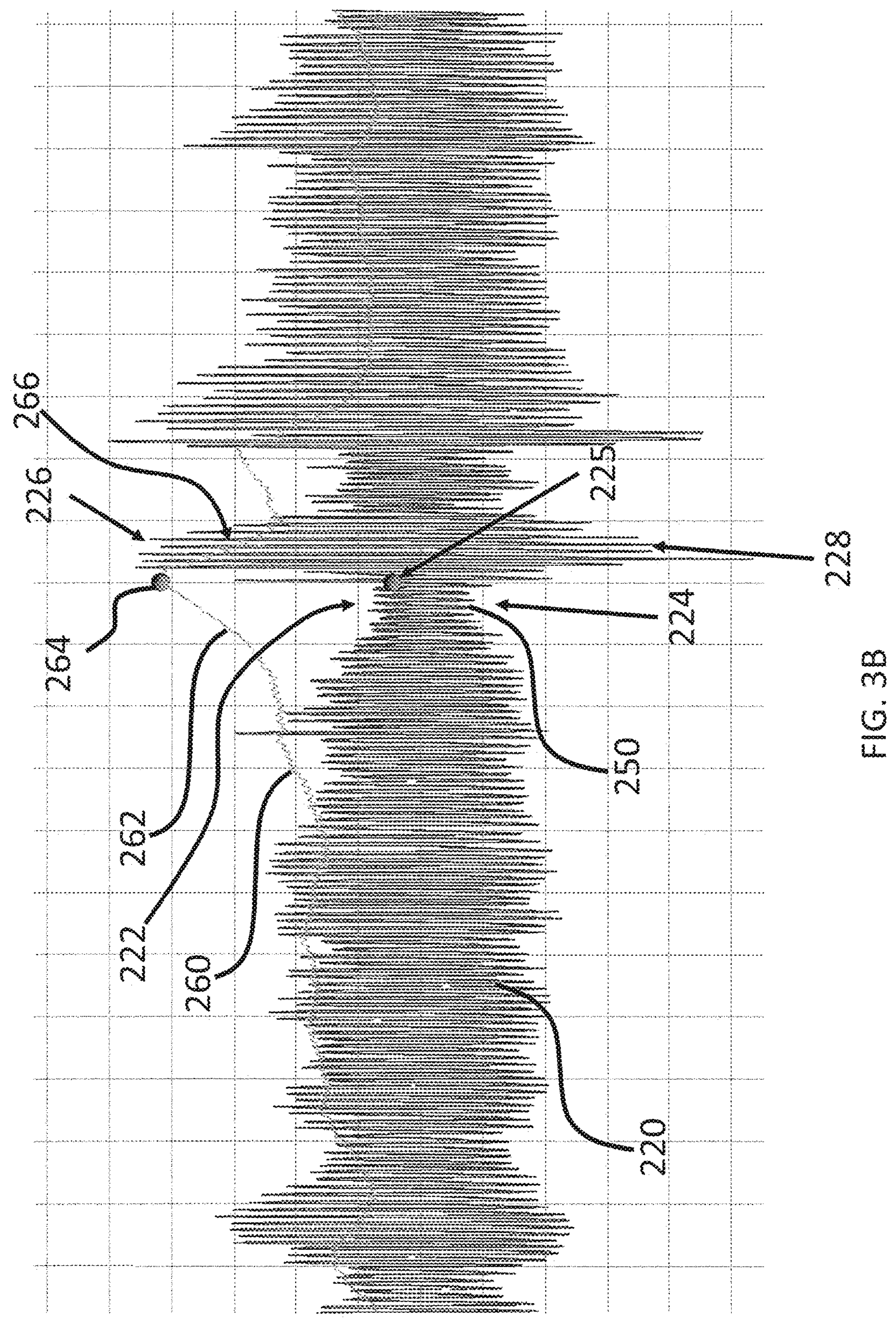
FIG. 3B illustrates an exemplary user's respiration signal and exemplary estimated blood $CO_2$ levels according to the method of FIG. 3A.

FIG. 3B illustrates an example user's flow signal 220 and example estimated blood $CO_2$ levels 260 with respect to time according to the method of FIG. 3A. FIG. 3B further shows the predicted events 250.

The relationship among the flow signal 220, the estimated blood $CO_2$ level 260 and/or the breathing events 250 can be seen in FIG. 3B. For example, hypopnea as indicated by a region of small-amplitude peaks 222 and small amplitude valleys 224 of the flow signal 220. The hypopnea can be preceded by and can coincide with a rise 262 in the estimated $CO_2$ level. The rise 262 of the estimated $CO_2$ level can culminate at a peak at the marker 264, when the user awakens and begins to draw deeper breaths, as shown by a region of larger-amplitude peaks 226 and larger-amplitude valleys 228 of the flow signal 220 after the marker 225. The deeper breaths can provide greater tidal lung volume for flushing the $CO_2$ from in the user's body and can therefore coincide with a decrease 266 and stabilizing of the estimated $CO_2$ level 260.

Example Applications of The Methods

Example applications of the methods described above will now be discussed. The methods described above can be run on-board the CPAP machine or other medical device. Blowers or flow generators of the CPAP machine or other medical device can be used to assist in adjusting therapy parameters. In some embodiments, the pressure can be increased or adjusted. In other embodiments, the pressure can be increased slowly to a predetermined level in cycles. The methods described above may also be run on separate devices.

Example Applications to Existing Therapies

Figure 4:
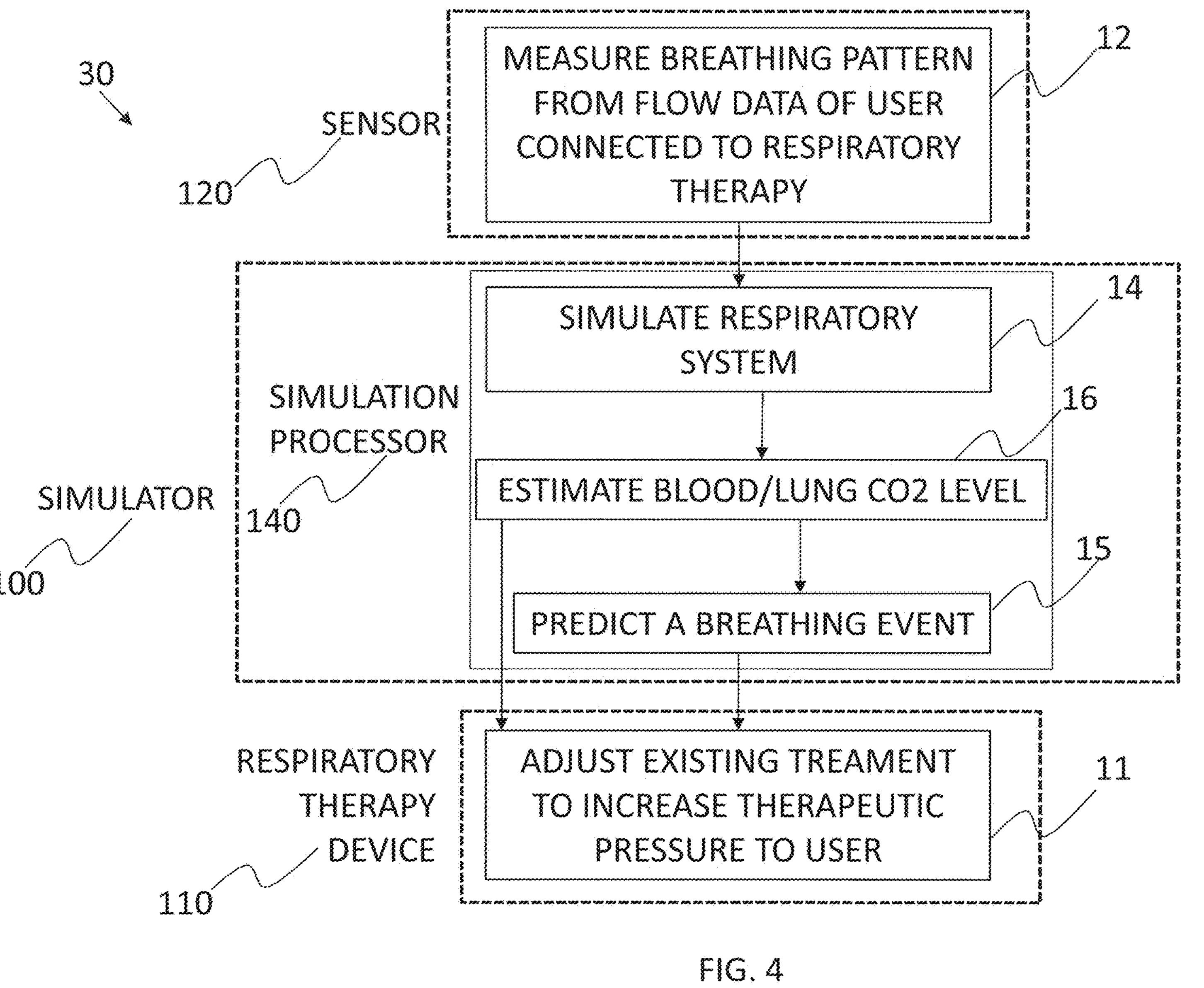
FIG. 4 illustrates a flowchart of an exemplary application of the methods of estimating $CO_2$ levels from a user's respiration signal of FIGS. 2 and 3A.

FIG. 4 illustrates an example application 30 of the methods 10, 20 shown in FIGS. 2 and 3A to influence existing treatments. As shown in FIG. 4, the simulator 100 can be operably coupled to the respiratory therapy device 100 that can provide therapeutic pressure to the user at an operating pressure of the respiratory therapy device 100. In this application, "operably coupled" can refer to devices being connected by one or more cables/wires, and/or wireless connections using any existing wireless technology. In addition to features of the methods 10, 20 as shown in FIGS. 2 and 3A, after predicting 15 the breathing event, the respiratory therapy device 110 can adjust and/or change 11 an existing treatment configuration based on the predicted breathing events. In some embodiments, the respiratory therapy device 110 can also adjust and/or change 11 an existing treatment configuration based on the estimated blood $CO_2$ level. Adjusting and/or changing 11 the existing treatment configuration can include increasing the operating pressure of the respiratory therapy device so that the user can receive a greater therapeutic pressure. For instance, when high $CO_2$ levels can be estimated and/or when hypopnea can be predicted, the respiratory therapy device 110 can increase its operating pressure. The greater therapeutic pressure delivered to the user can attempt to further open the user's airway and to induce deeper breathing.

Variable Ventilation—Ramp Cycle Therapy Example

Figure 5A:
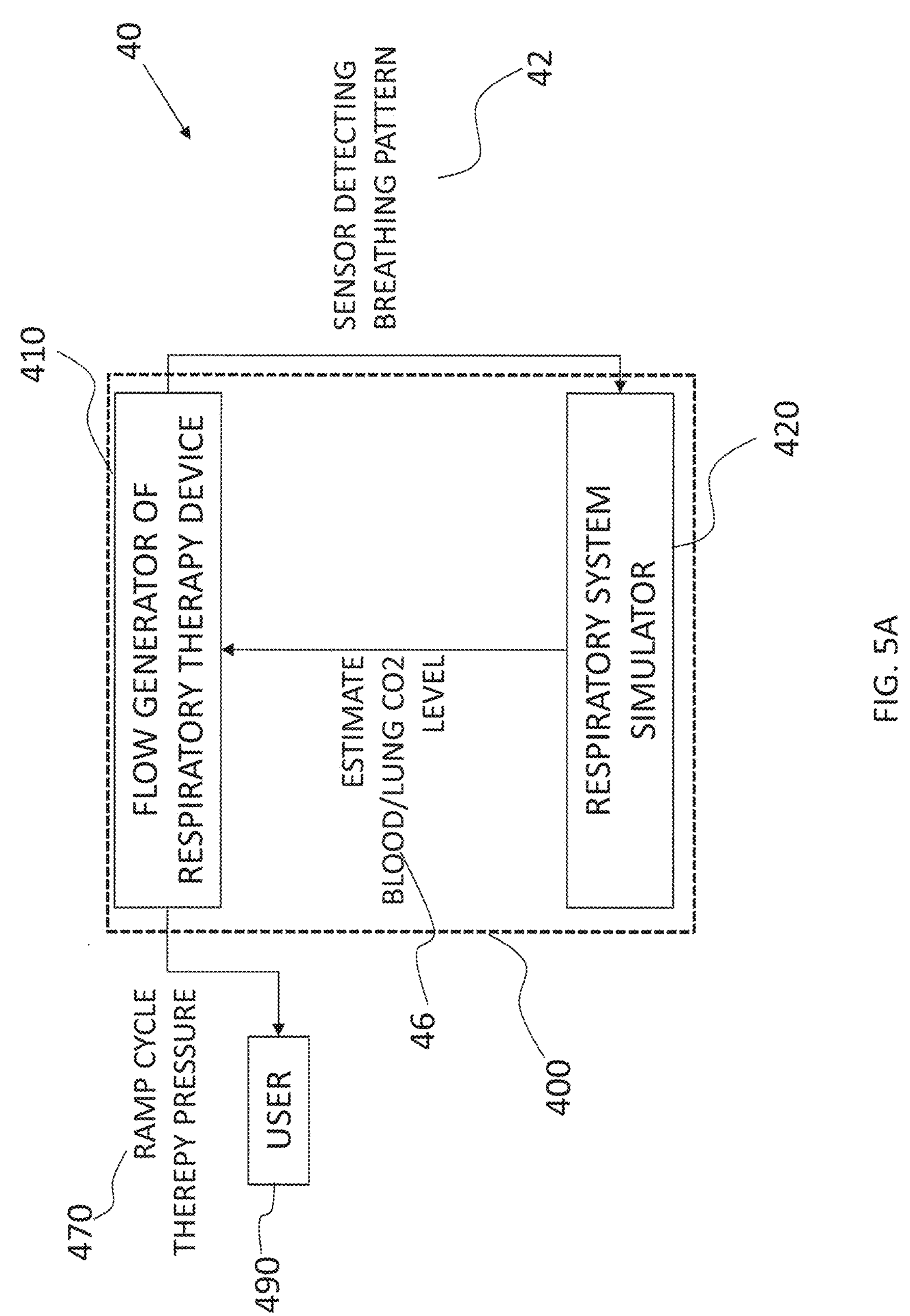
FIG. 5A illustrates a flowchart of an exemplary application of the methods of estimating $CO_2$ levels from a user's respiration signal of FIGS. 2 and 3A using a ramp cycle therapy.

FIG. 5A illustrates an example ramp cycle therapy 40 which may provide a greater rate of flushing of $CO_2$ from the user's lungs. As described above, one or more sensors can detect 42 a respiration signal from the respiratory therapy device 400 connected to the user 490 or directly from the user 490 as described above. For example and not by way of limitation, the respiration signal can be flow data. A respiratory system simulator 420 can use the respiration signal from the sensor(s) to simulate the user's metabolic rate. In the illustrated embodiment, the simulator 420 can estimate 46 the user's lung or blood $CO_2$ level as an output. In other embodiments, other indicators of the user's metabolic rate can be estimated. The flow generator of the respiratory therapy device 410 can be controlled based on the estimated lung or blood CO, level. The flow generator of the respiratory therapy device 410 can generate a ramp cycle therapy pressure 470 based on the estimated lung or blood $CO_2$ level (and/or predicted breathing events). The ramp cycle therapy pressure 470 can cyclically rise above an operating pressure of the respiratory therapy device 410 to attempt to increase a volume of the user's lungs for flushing $CO_2$ from the user's lungs and subsequently fall to the operating pressure more rapidly than the rise in pressure, for example during one exhalation, thereby advantageously reducing an abnormally high $CO_2$ level. With the ramp cycle therapy, the effective increase in the $CO_2$ flushing volume of the user's lungs can be about 5% to about 15% depending on the rate of increase and a volume of the user's lungs for flushing the $CO_2$.

Details of the ramp cycle therapy 40 will now be described. The ramp cycle therapy can, in some examples, be based on a principle that introducing a higher proportion of ambient air into the lungs can dilute the concentration of $CO_2$ in the lungs, as the $CO_2$ concentration of ambient air (0.4%) is much lower than a typical lung $CO_2$ concentration. In some embodiments, the $CO_2$ concentration of ambient air can be about 0.4% and the lung $CO_2$ concentration can be about 5%, or higher if $CO_2$ levels have built up over time.

Further, introducing the higher volume of ambient air into the lungs could result in more air being expelled from the lungs when the therapy pressure 470 is reduced to the operating pressure. Whenever an additional volume of air is expelled, the lung $CO_2$ concentration can be reduced by between about 5-15% from the initial concentration, depending on the flushing volume. Repeated flushing of the lungs with ambient air could prevent or mitigate the $CO_2$ build-up in the lungs and advantageously prevent a sleep disordered breathing event from occurring.

In some embodiments, the ramp cycle therapy 40 could be initiated by the respiratory therapy device 400 when the estimated $CO_2$ levels are above a threshold, are increasing, or are increasing above a predetermined rate. In other embodiments, the ramp cycle therapy 40 could run continuously throughout the therapy over and above a set point pressure or therapeutic pressure as determined by other algorithms. In one embodiment, the algorithm can be an auto PAP algorithm, which can change pressure provided to the patient after detecting the breathing events. A rate of increase, an amplitude, and/or a frequency of the ramp cycle therapy pressure may be adjusted based on the estimated $CO_2$ levels as described above. In some embodiments, the ramp cycle therapy may be used with other methods of measuring or estimating $CO_2$ levels.

Further, the user's lung compliance can affect the ramp cycle therapy. The lung compliance can be defined as an ability of the user's lungs to stretch and expand. The lung compliance of the user can be determined over time through therapy data. In some embodiments, the lung compliance of the user can be determined by looking at the exhalation volume at the end of each ramp cycle and by determining how much the increase in pressure contributed to an increase in lung volume. The respiratory therapy device 400 can dynamically update the user's lung compliance to create a more accurate ramp cycle therapy 40. In a non-limiting example, if the therapy data determines that the lung's ability to stretch is lower than an assumed amount for each cm $H_2O$ increase in pressure, the increase in the ramp cycle therapy pressure 470 over the set point pressure may be increased to compensate for the lower lung compliance.

Figure 5B:
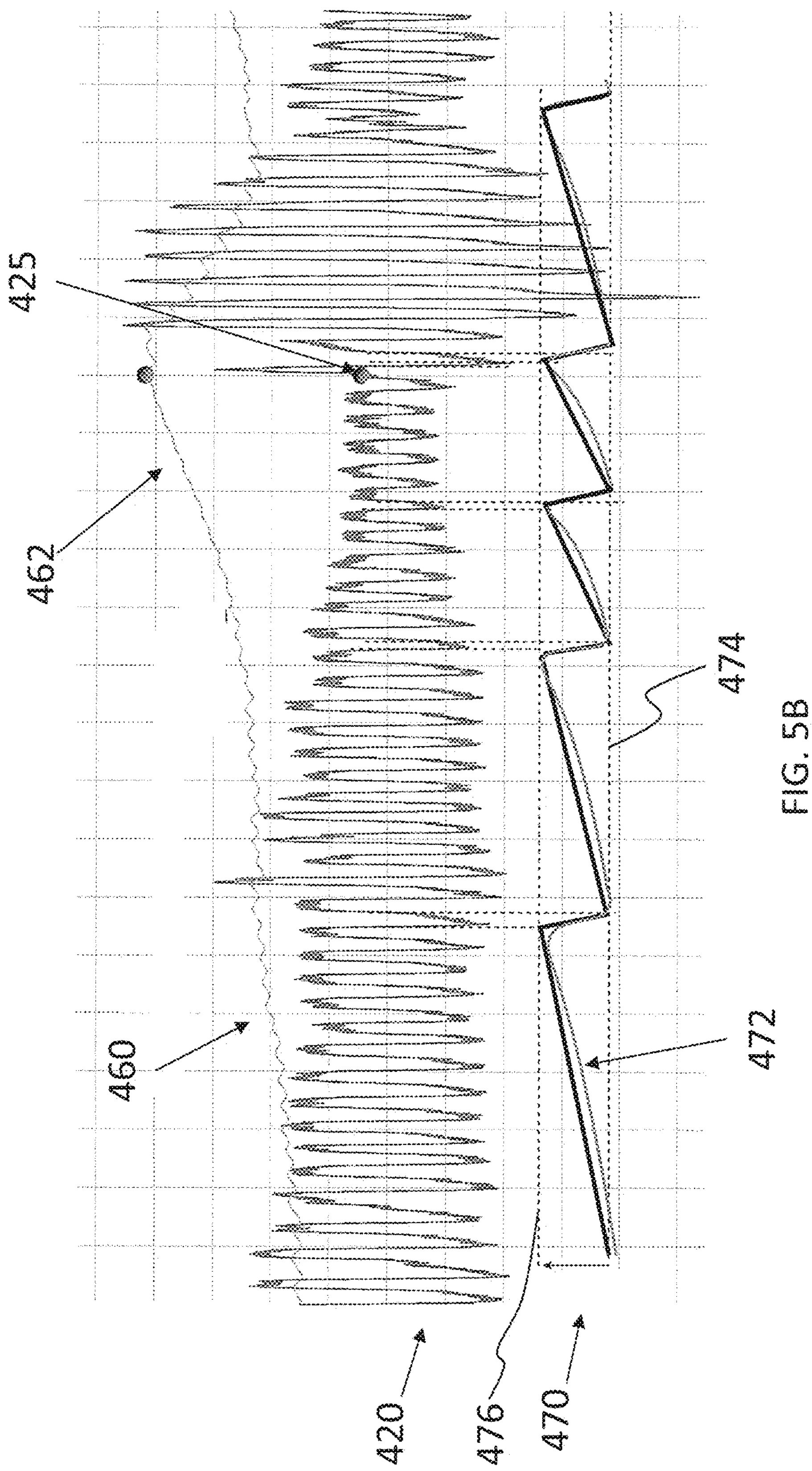
FIG. 5B illustrates an exemplary user's respiration signal, exemplary estimated blood CO2 levels and exemplary ramp cycle therapy pressure of FIG. 5A.
Figure 6:
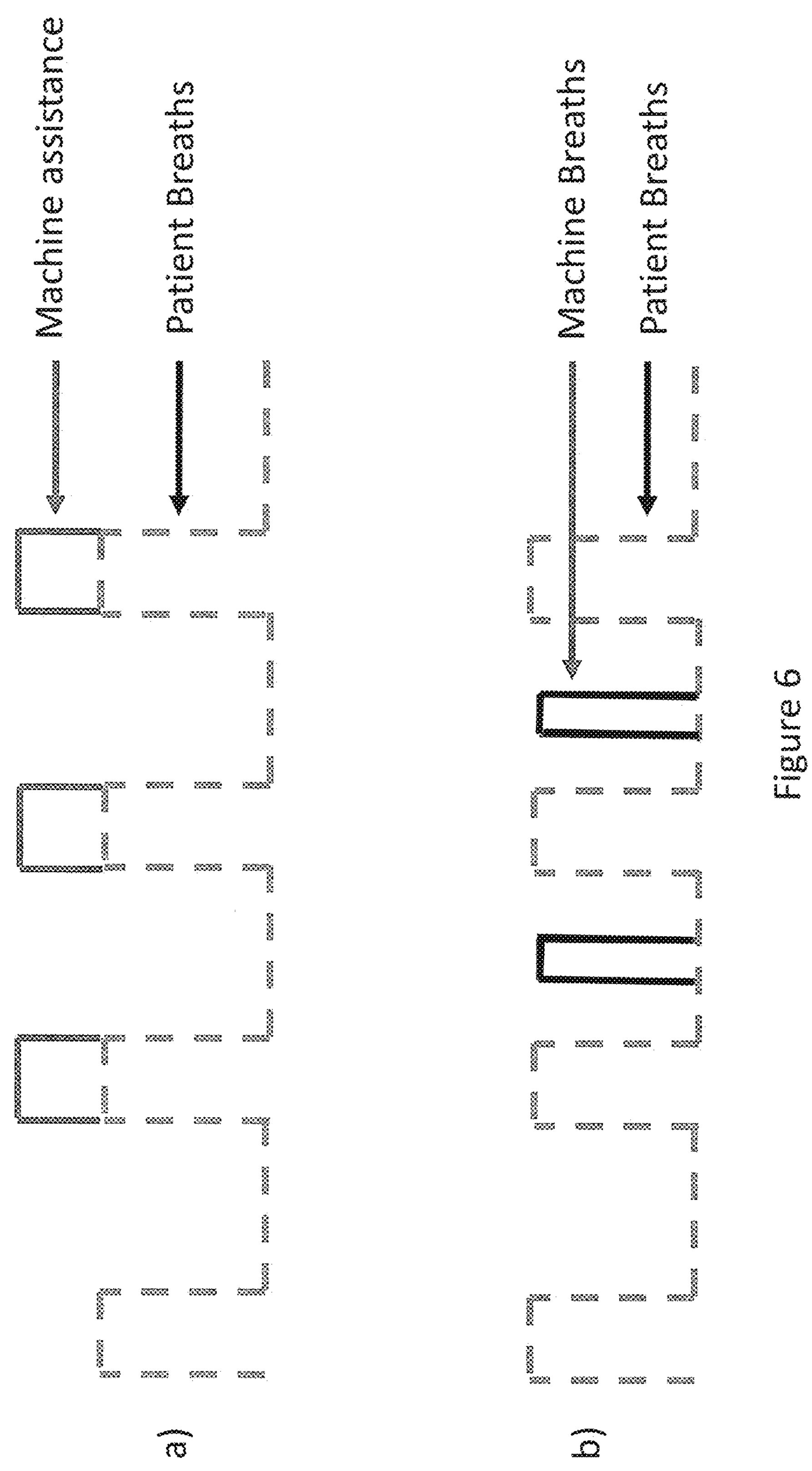
FIG. 6(*a*) illustrates an exemplary user's respiration signal in dashed line, with the solid line indicating the ventilatory assistance provided by a prior art respiratory therapy system.
Figure 7:
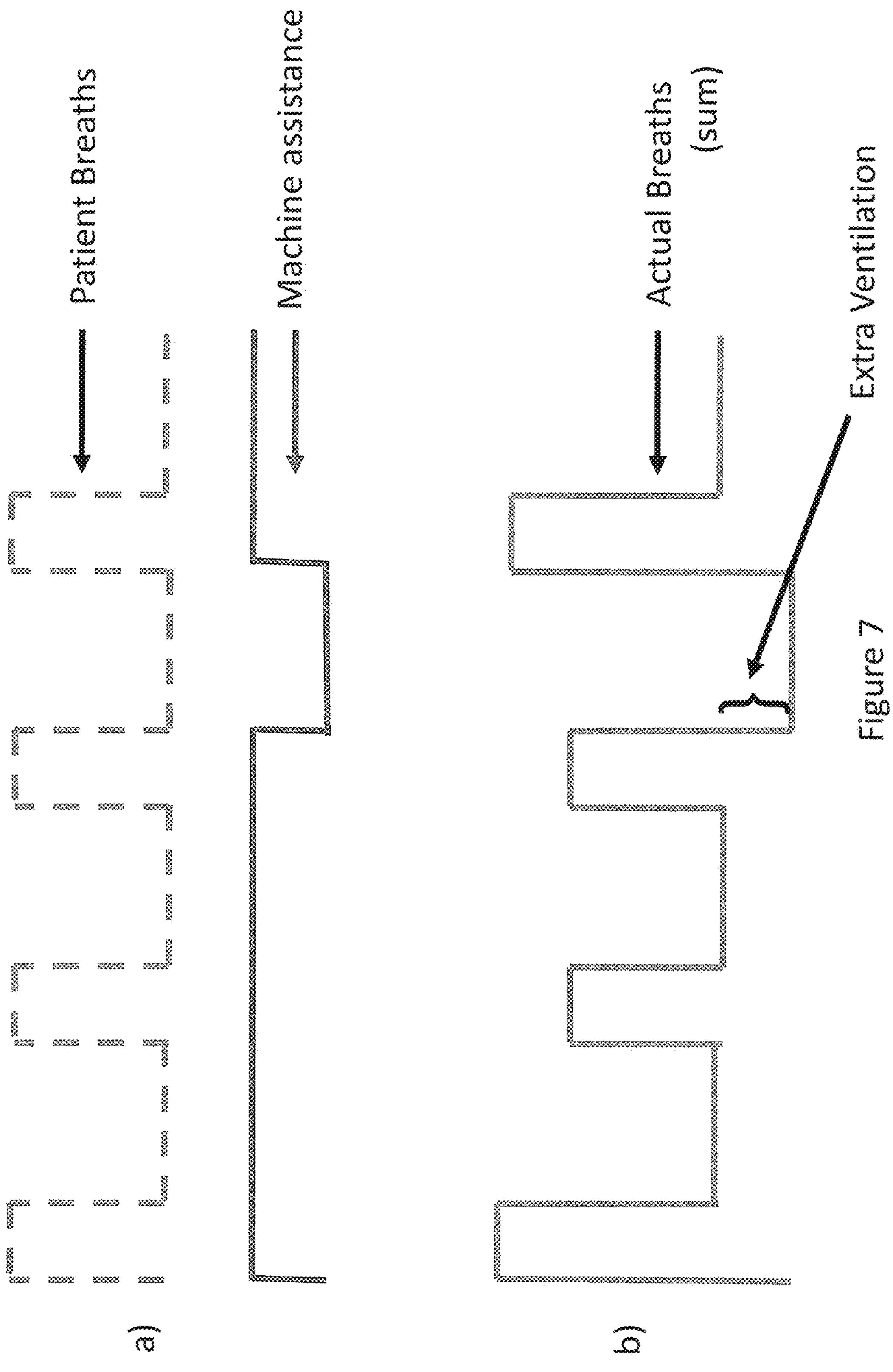
FIG. 7(*a*) illustrates an exemplary user's respiration signal in dashed line, with the solid line indicating the ventilatory assistance provided by a respiratory therapy system in accordance with the current disclosure.
Figure 8:
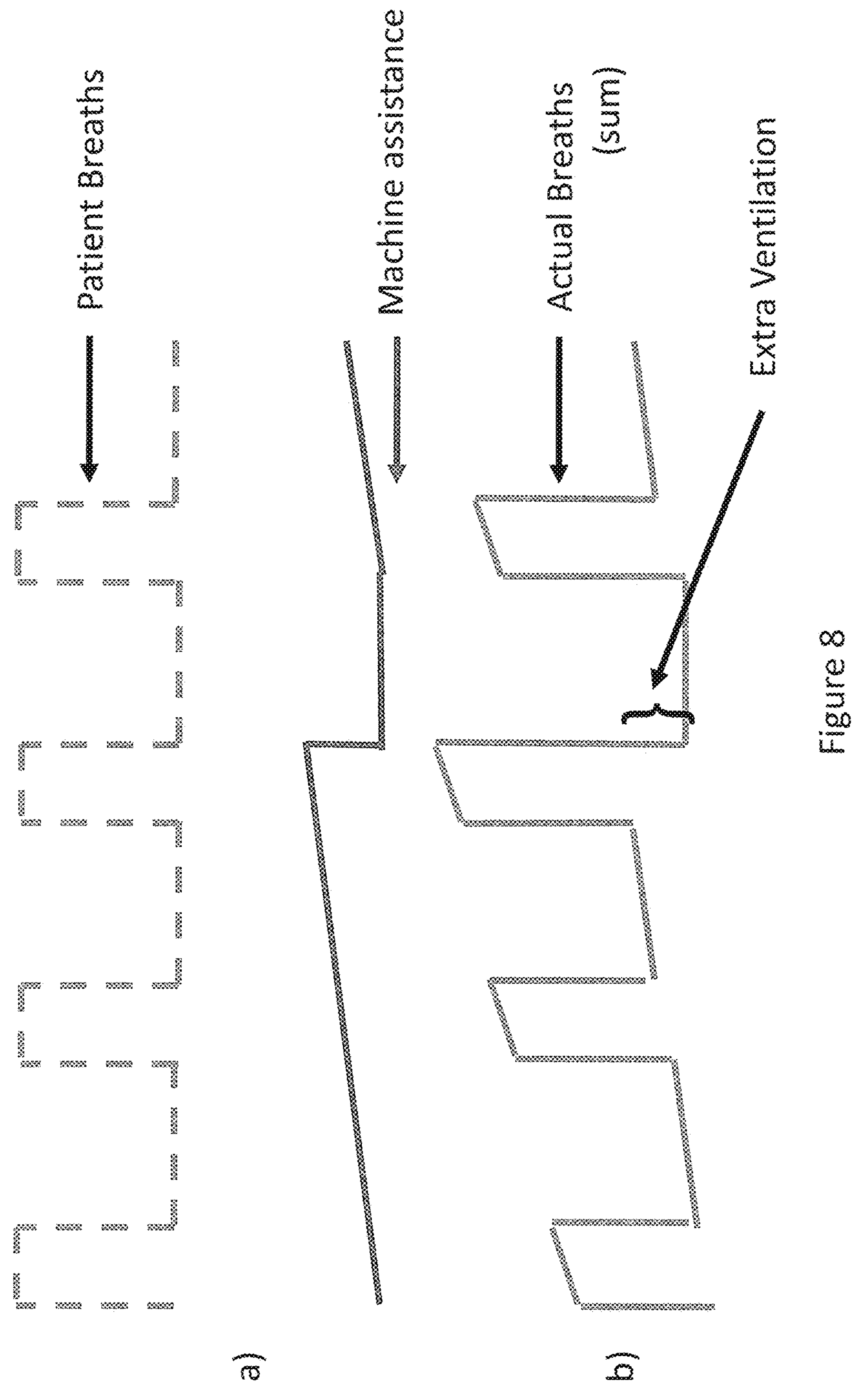
FIG. 8(*a*) illustrates an exemplary user's respiration signal in dashed line, with the solid line indicating the ventilatory assistance provided by a respiratory therapy system in accordance with the current disclosure.

As described above, the ramp cycle therapy pressure 470 can be provided in cycles. In other embodiments, the ramp cycle therapy pressure 470 can have other variations and/or patterns. FIG. 5B illustrates an example waveform of the ramp cycle therapy pressure 470. The waveform on the left of the marker 425 indicates a user's respiration signal when the user is sleeping and the waveform on the right of the marker 425 indicates the respiration signal after the user wakes up as a result of the sleep disordered breathing event. As shown in FIG. 5B, the ramp cycle therapy pressure 470 can be a sawtooth wave, gradually ramping upwards and then dropping sharply. The ramp cycle therapy pressure 470 can have an increase 472 from a first threshold 474 to a second threshold 476 over a predetermined number of breaths taken by the user. The increase can be one or more of linear, exponential, stepped function increases, or a combination thereof. The thresholds can depend on the therapeutic pressure set by the clinician. For example and not by way of limitation, the therapeutic pressure set by the clinician can be in the range of 4-20 cm $H_2O$. This therapeutic pressure may also change throughout the therapy in response to the breathing events such as apneas and the like. When an apnea is sensed, the respiratory therapy device can increase the therapeutic pressure as described above. In some embodiments, the first threshold can be the therapeutic pressure. The second threshold can be between about 1 and about 5 cm $H_2O$ above the therapeutic pressure. The ramp therapy can be seen as slow ventilation over a number of breaths over and above the set CPAP therapeutic pressure. In some embodiments, the first threshold 474 can be about 0 cm $H_2O$ and the second threshold 476 can be about 4-6 cm $H_2O$. In some embodiments, the increase 472 of pressure can increase the volume of the user's lungs by approximately 100 mL/cm $H_2O$. For example, the increase 472 from about 0 to about 5 cm $H_2O$ can increase the volume of the lungs for flushing the $CO_2$ by about 0.5 L. One of ordinary skill in the art would appreciate that the increase in the volume of the user's lungs may vary. In some embodiments, each ramp cycle can increase the pressure by about 3 to about 5 cm $H_2O$, thereby increasing the lung volume by about 300 to about 500 ml. Further, the increase 472 can stop when the ramp cycle therapy pressure 470 reaches the second threshold 476. The ramp cycle therapy pressure 470 can return to the first threshold 474 during an exhalation phase of one breath. When the pressure is rapidly dropped back to the first threshold 474 during exhalation, the additional volume of air in the lung can be exhaled. This exhalation can flush the lung. Dropping the ramp cycle therapy pressure 470 over one breath can minimize opportunities for $CO_2$ to build up in the decreasing lung volume and ensures more flushing of the lungs. In other embodiments, the return to the first threshold 474 could be over more than one breath. In a non-limiting example, the return to the first threshold 474 can be over two breaths.

The ramp cycle therapy 40 can use the estimated blood $CO_2$ level (and/or the predicted breathing events) to adjust a rate of the increase 472 of the ramp cycle therapy pressure. If an increased risk of a breathing event is predicted from the $CO_2$ level, the increasing pressure phase 472 of the ramp cycle may be adjusted to occur over a reduced number of breaths. In a non-limiting example, the ramp cycle can be reduced to 5 breaths from 10 breaths. A shorter ramp cycle can advantageously provide more effective and frequent flushing and to bring down the lung $CO_2$ level in advance of a breathing event, thereby preventing the breathing event from occurring or mitigating the breathing events. For example, as shown in FIG. 5B, the increase 472 can be from about 0 to about 5 cm $H_2O$ over a course of about 12-13 breaths when the estimated blood $CO_2$ level 460 can be substantially constant or normal. When the estimated blood $CO_2$ level begins to rise 462, the rate of the increase 472 can be higher so that the ramp cycle therapy pressure 470 can rise from the first threshold 474 to the second threshold 476 in fewer breaths. For example and not by way of limitation, the ramp cycle therapy pressure 470 can rise from the first threshold 474 to the second threshold 476 in about five to six breaths of the user.

Adjusting a length of the ramp cycle based on the estimated $CO_2$ level (and/or the predicted breathing events) can advantageously allow the ramp cycle therapy pressure 470 to be controlled with respect to the user's respiratory cycle. That control may be such as to control some or all of the ramp cycle therapy to be asynchronous with a particular phase or part of a user's respiratory cycle. That control may be such as to control some or all of the ramp cycle therapy to partially synchronize, or to fully synchronize, with some or all of the user's actual respiratory cycle and to mitigate effects of the breathing events. Broadly, the ramp cycle may be controlled so as to begin in synchrony with the start of an inspiratory portion of a breath, to continue for more than one breath, and to end during an expiratory portion of a breath. For example and not by way of limitation, the effects of the breathing events can include a rise 462 in the blood $CO_2$ level when there is hypopnea. A hypopnea may also be preceded by a rise in the $CO_2$ level. As shown in FIG. 5B, the shorter ramp cycle 478 can be delivered, for example, when a hypopnea is detected and/or predicted. The blood $CO_2$ level can decrease after the shorter ramp cycle because more $CO_2$ can have been flushed from the user's body. The more effective increase in the therapeutic pressure can also induce the user to deeper breaths.

In other examples, the ramp cycle may be controlled by time or rate so as to be independent of any particular number of breathing cycles. Thus, the ramp cycle may be controlled to provide approximately two to 10 cycles per minute, regardless of how many breathing cycles occur during that time. More preferably the ramp cycle may be controlled to provide approximately three to six cycles per minute, and in some cases three to four cycles per minute.

In examples where the pressure drop is triggered by expiration so as to drop at the start of, or at least during, an expiratory portion of a breath, the variable ventilation profile may be controlled to automatically trigger the pressure drop in the event of a time out or period in which expiration should have started but has not. Thus, the profile may be such as to automatically initiate the pressure drop after a set or predetermined time period, even if expiration has not actually begun.

Asynchronous, Partially Synchronous and Fully Synchronous Variable Ventilation

With additional reference to FIGS. 6 to 9, further methods of providing respiratory therapy are provided using some of the principles described above. For example, some examples provide variable ventilation using a ramp cycle similar to those discussed above in relation to FIGS. 5A and 5B. Others examples of variable ventilation in accordance with this disclosure use a cycle incorporating a single or multiple stepped change between first and second pressure thresholds. The methods of FIGS. 5A and 5B, and FIGS. 7A to 9B control the flow of breathable gas to the user such that the pressure is increased from first to second pressure thresholds over multiple sequential breathing cycles, and subsequently reduced from the second to the first pressure thresholds during expiration. Thus, for example, the pressure may be increased over three or four breaths, and then dropped over a single expiration.

In these examples a respiratory therapy device, for example as described above, is configured to supply a flow of breathable gas to a user via a breathing gas delivery conduit and a patient interface; and comprises a controller configured to control a pressure of the gas supplied to the user; and one or more sensors configured to measure data relating to a patient's breathing pattern. The controller is configured to control the device to increase the pressure of the breathable gas supplied to the user from a first pressure to a second pressure over a predetermined number of breaths. The controller is further configured, after the second pressure is reached or maintained, to decrease the pressure of the gas supplied to the user from the first pressure to the therapeutic pressure during one or more periods of exhalation.

In these examples, variable ventilation is achieved by the increase in pressure from the first to second pressure thresholds and this can be asynchronous with the breathing cycle of the patient in the sense that delivery of the increased and/or decreased pressure need not be synchronized with the start of inspiration or expiration. In these examples, the total ventilation does not always follow the pattern of natural breaths of the user, as it is only the total amount of gas moved in and out that determines the elimination of $CO_2$. Thus any cyclic change in volume (including the resting FRC) will accomplish some ventilation and contribute to the clearance of $CO_2$.

A variable ventilation profile, examples of which are described above and below, may itself comprise a sole ventilation profile providing assisted ventilation to the user, or may be superimposed with one or more further ventilation profiles so as to provide a composite ventilation profile to the user. In the latter example, the variable ventilation profile may form a baseline ventilation profile which may be supplemented by one or more further profiles.

As mentioned above, examples of conventional breathing modes include:

1. Total controlled ventilation—the respiratory therapy device delivers a set number of fixed volume or pressure cycles that determine total ventilation without regard for patient efforts. This is often used on paralyzed or deeply sedated subjects, but is generally uncomfortable in conscious patients.
2. Intermittent mandatory ventilation (IMV)—the respiratory therapy device delivers fixed numbers of volume or pressure cycles that cause a minimum number of controlled or augmented breaths, mixed in with spontaneous breaths initiated by the patient. However, between each breath (including the mandatory breaths) the patient is allowed to return to FRC.

3. Backup ventilation or rate—the respiratory therapy device switches to total controlled ventilation when the patient experiences either a respiratory pause of a pre-set duration, or when the total average ventilation falls below a pre-set level. At other times, the patient is allowed to breathe at will.
4. Assisted ventilation (e.g. pressure support)—the respiratory therapy device, on a patient triggered breath, delivers a set amount of additional volume, pressure or some combination.

These modes are all based on providing individual breaths at a frequency generally in the range of 10-25/min, with return to FRC between breaths.

Respiratory therapy methods and devices in accordance with the present disclosure may be operative according to an algorithm configured to provide variable ventilatory assistance which combines existing spontaneous ventilation (or any of the above continuous cyclic modes of synchronous mechanical assistance) with a background variable profile of relatively slow artificial breaths that are created by slowly inflating the lung over multiple spontaneous breaths and then allowing the lung to empty down to FRC. This can also be described as slowly (e.g. 2-5 L/min) increasing the FRC and then allowing the lung to deflate passively, without relationship to the spontaneous breathing pattern. This variable ventilation is thus independent of spontaneous breaths/tidal volumes and contributes an independent and predictable amount of respiratory therapy device driven ventilation to the total ventilation received by the user. The remainder of ventilation can be supplied by the spontaneous breathing of the patient or by conventional ventilator modes acting at a different rate that enlarge breaths or provide additional breaths.

With reference to FIGS. 6A and 6B, these illustrate prior art assisted ventilation in which spontaneous regular breathing shown in dotted line is supplemented with machine assistance shown in solid line. FIG. 6A shows a ventilation profile which provides assistance to the size of each tidal volume (e.g. pressure support). FIG. 6B shows a ventilation profile that provides extra breaths (backup frequency) in between the user's breaths.

With reference to FIGS. 7A and 7B, a variable ventilation profile is shown of a respiratory therapy method or device in accordance with the present disclosure. In this example, variable ventilation, shown in solid line, is provided in which a single stepped pressure increase from a first pressure threshold to a second higher pressure threshold is provided. Pressure is maintained at the second, higher pressure threshold for a predetermined number of breath cycles and then controlled to drop back to the lower first pressure threshold during a single expiration. This ventilation profile therefore comprises a relatively slow cycle with a relatively long inspiratory period during which ventilatory assistance is provided at the second pressure threshold, and a relatively short withdrawal of ventilatory assistance during expiration to allow the lungs to drop to FRC between asynchronous breaths. FIG. 7B shows the sum of patient spontaneous patient breaths and asynchronous breaths resulting in total ventilation to the user, which is potentially greater than user spontaneous ventilation. In this example the first pressure, and the second pressure, are constant over multiple cycles of the ventilation profile. In this example, the pressure increase is timed to begin at the start of an inspiratory cycle, to continue for multiple breaths, and the pressure drop is timed to begin at the start of an expiratory cycle, after the predetermined number of multiple breaths.

With reference to FIGS. 8A and 8B, another ventilation profile is shown of a respiratory therapy method or device in accordance with the present disclosure. In this example, variable ventilation, shown in solid line, is provided in which there is a single, relatively gradual, ramped pressure increase from a first pressure threshold to a second higher pressure threshold, similar to the ramped ventilation profile of FIG. 5B. The pressure increases from the first pressure threshold over a number of breath cycles. Once the pressure reaches the second, higher pressure threshold, pressure is then controlled to drop back to the lower first pressure threshold during a single expiration. In this example at least one of the first pressure, and the second pressure, are constant over multiple cycles of the ventilation profile. This ventilation profile therefore comprises a relatively slow ramping cycle of FRC with a relatively long increase time and a relatively short withdrawal of assistance to allow the lungs to drop to FRC between asynchronous breaths. The sum of patient spontaneous patient and asynchronous changes in FRC results in total ventilation which is potentially greater than patient spontaneous ventilation. In this example, the pressure increase is timed to begin at the start of an inspiratory cycle, to continue increasing for multiple breaths, and the pressure drop is timed to begin at the start of an expiratory cycle, after the predetermined number of multiple breaths.

With reference to FIGS. 9A and 9B, a further ventilation profile is shown of a respiratory therapy method or device in accordance with the present disclosure. In this example, variable ventilation, shown in solid line, is provided in which a plurality of stepped pressure increases are provided from a first pressure threshold to a second higher pressure threshold. Pressure is increased in steps over a number of breath cycles, and is maintained at the second, higher pressure threshold for a predetermined time period which may be a proportion of a breath cycle, a single breath cycle, or over a predetermined plurality of breath cycles. Pressure is then controlled to drop back to a lower pressure during a single, or small number of, expiration period(s). The lower pressure may be the first pressure threshold or may be a pressure higher than the first pressure threshold and lower than the second pressure threshold. This ventilation profile therefore provides variable, partially synchronous, ventilation in a relatively slow cycle with a relatively long inspiratory time and a relatively short withdrawal of assistance to allow the lungs to drop to FRC between asynchronous breaths, similar to the profile of FIGS. 8A and 8B. However, in this example, increases in FRC are accomplished with individual step rises in pressure support timed with inspiration (IPAP), instead of a continuous increase in pressure, cycled with progressive rises in end-expiratory pressure (EPAP) that prevent full exhalation. The sum of spontaneous patient breaths and asynchronous ventilation results in total ventilation which is potentially greater than patient spontaneous ventilation. In this example, each stepped pressure increase is timed to begin at the start of an inspiratory cycle, to continue increasing for multiple breaths, and the pressure drop is timed to begin at the start of an expiratory cycle, after the predetermined number of multiple breaths.

The variable ventilation comprising part of the current disclosure may include any one or more of the following benefits:

1. Timing of mechanical breathing assistance is less dependent on detecting user efforts, which can be a problem in non-invasive mask ventilation.
2. Small cycles of changing FRC may be imperceptible to the user, and thus more comfortable than large breaths continuously. This may help to reduce arousals during sleep.
3. Slowly changing FRC may inhibit breathing (this is known as the Hering Breuer reflex) less than continuous large changes in volume from larger breaths. As a result the user may then continue to provide their own ventilatory efforts fully, rather than being suppressed as mechanical ventilatory support is added.
4. Slowly varying cyclical changes in FRC can be combined with other types of ventilation such as CPAP, bi-level and timed modes of ventilation, as well as modes that detect the awake state of the user and turn ventilation on and off with arousal. Ventilation in accordance with the current disclosure may therefore comprise a secondary or base line ventilation which can be supplemented with, and superimposed with, other types of ventilation to provide a composite ventilation to the patient.
5. Because changes in the pressure provided by the asynchronous assistance are relatively slow and thus minimally affect the waveform of inspiration within a single breath, algorithms that are dependent on inspiratory shape (e.g. detection of flow-limitation in autoCPAP) can function with little modification and less corruption than during large pressures used to assist breath size externally.

It will be appreciated that the above disclosure incorporates any type of ventilation profile which provides an increase in pressure over a plurality of, or at least more than one, breathing cycles, and which reduces the pressure more quickly, that is, in less time than the duration of the pressure increase. In some examples, the pressure is decreased over a single expiratory cycle. Thus, in some embodiments, the pressure may be increased rapidly, maintained over multiple breathing cycles, and dropped quickly. In other embodiments, the pressure may be increased slowly over multiple breathing cycles and then dropped quickly. The start and end pressures during the increasing pressure phase may be kept constant, or may increase or otherwise vary over successive cycles of the ventilatory profile. For example, the second pressure to which the pressure is increased may itself increase over successive cycles. Likewise the first pressure to which the pressure drops during expiration may increase over successive cycles. Further, a combination of one or more stepped and/or ramped pressure changes may be used during one or both of the pressure increase and decrease phases.

Figure 9:
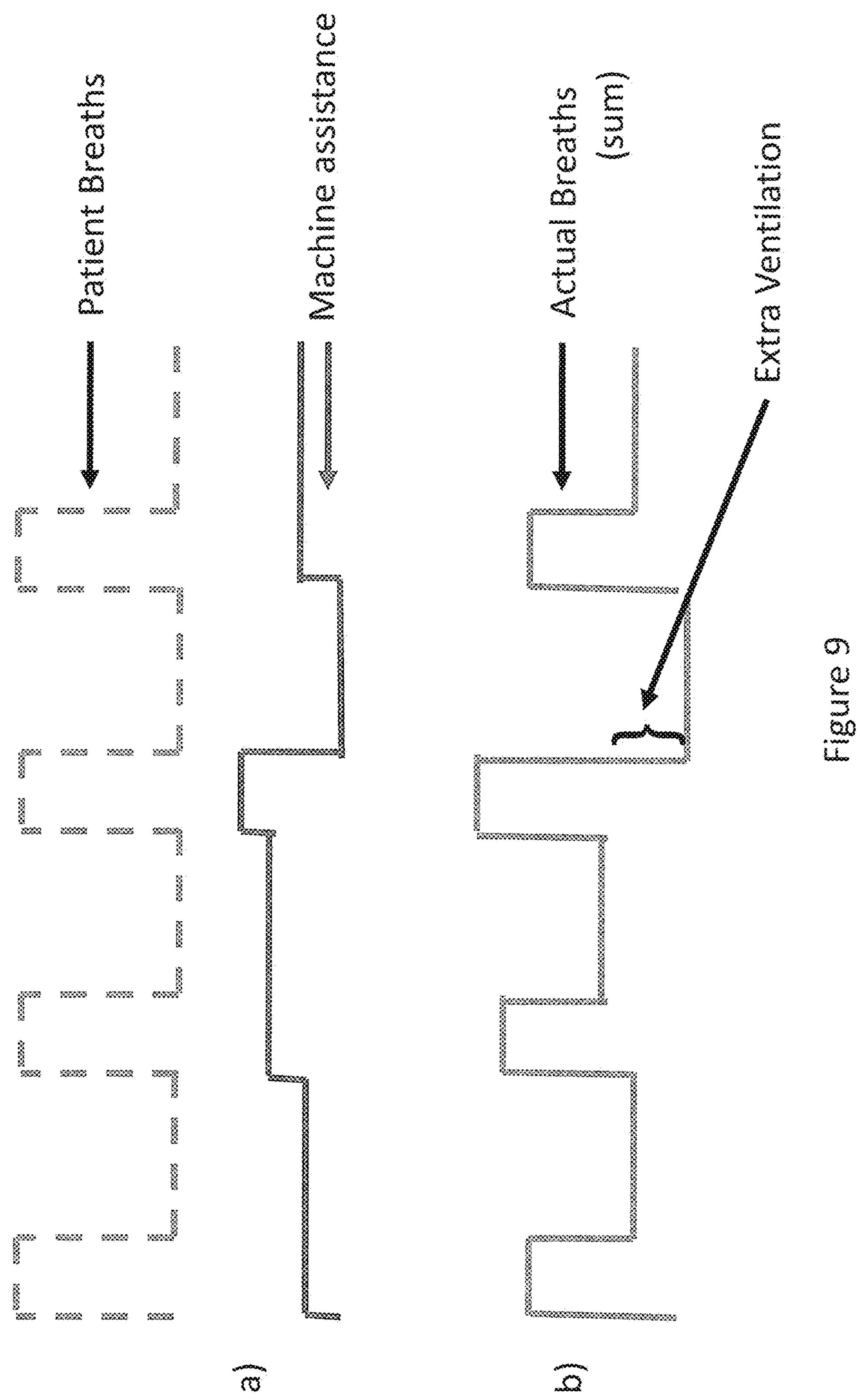
FIG. 9(*a*) illustrates an exemplary user's respiration signal in dashed line, with the solid line indicating the ventilatory assistance provided by a respiratory therapy system in accordance with the current disclosure.

A further example of a variable ventilation profile in accordance with the current disclosure is similar to the stepped increase described with reference to FIG. 9, is a profile in which pressure is increased over each inspiration and subsequently paused during at least one expiration. Thus, the pressure continues to increase over sequential breathing cycles, but is held constant during each, or at least some, expiration period(s).

Another example of a variable ventilation profile in accordance with the current disclosure incorporates a variation to one or both of the pressure increase and pressure decrease to account for the awake/asleep state of the patient. The ventilation profile may therefore be configured to reduce the magnitude of, the rate of change of, pressure between the first and second pressures, or to alter the first and second pressures, if the patient or user is determined to be awake.

Whilst the above examples discuss ventilation profiles based on pressure control, whereby a controller of a respiratory therapy device is configured to control the pressure of breathable gas supplied to the user, the disclosure includes similar ventilation profiles based on flow control, whereby a controller of a respiratory therapy device is configured to control the flow of breathable gas supplied to the user. Suitable pressure and/or flow sensors and/or control algorithms may be provided accordingly. In any of the above examples and/or ventilation profiles the control of the ventilation profile by the or each controller is automatic in that it may occur without any patient intervention or external input, and/or may be recurring for any time duration required and/or for any number of breathing cycles required.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A respiratory therapy device configured to supply a flow of breathable gas to a user via a breathing gas delivery conduit and a non-sealed patient interface to provide nasal high flow therapy, the device comprising:

a controller configured to control a flow of the breathable gas supplied to the user via the non-sealed patient interface; and wherein the controller is configured to control the device according to a variable ventilation profile to repeatedly:

increase a flow rate of the breathable gas supplied to the user from a first flow rate to a second flow rate over a predetermined number of breaths, the predetermined number of breaths being adjusted responsive to a characteristic of a breathing pattern of the user; and in response to the second flow rate being reached or maintained for a predetermined period of time, decrease the flow of the breathable gas supplied to the user from the second flow rate to the first rate during one or more periods of exhalation.

2. The device of claim 1 wherein the increased flow rate is supplied asynchronously with the breathing pattern of the user, wherein a timing of the increased flow rate is not synchronous with inspiratory and/or expiratory phases of the breath.

3. The device of claim 1 wherein the increased flow rate is supplied semi-synchronously with the breathing pattern of the user, wherein a timing of the increased flow rate is synchronous with part of inspiratory and/or expiratory phases of the breath.

4. The device of claim 1 wherein the increased flow rate is supplied synchronously with the breathing pattern of the user, wherein a timing of the increased flow rate is synchronous with inspiratory and/or expiratory phases of the breath.

5. The device of claim 1, wherein the controller is configured to control the device to increase the flow rate of the breathable gas supplied to the user from the first flow rate to the second flow rate via a single step increase from the first flow rate to the second flow rate.

6. The device of claim 1, wherein the controller is configured to control the device to increase the flow rate of the breathable gas supplied to the user from the first flow rate to the second rate via a plurality of step increases from the first flow rate to the second flow rate.

7. The device of claim 1, wherein the controller is configured to control the device to increase the flow rate of the breathable gas supplied to the user from the first flow rate to the second flow rate via at least one ramped increase from the first flow rate to the second flow rate.

8. The device of claim 7 wherein the controller is configured to control the device to increase the flow rate of the breathable gas supplied to the user from the first flow rate to the second flow rate via a plurality of ramped increases from the first flow rate to the second flow rate.

9. The device of claim 1, wherein a magnitude of the first flow rate increases over successive cycles.

10. The device of claim 1, wherein a magnitude of the second flow rate increases over successive cycles.

11. The respiratory therapy device of claim 1, further comprising one or more sensors configured to measure data relating to the user's breathing pattern, wherein the one or more sensors are configured to measure at least one respiration signal of the user, the at least one respiration signal indicative of any one or more of flow rate or thoracic movement of the user.

12. The respiratory device of claim 11 wherein the at least one respiration signal is indicative of any one of:

a. an onset, duration and/or end of inspiration;

b. an onset, duration and/or end of expiration; or c. a rise in a $CO_2$ level by estimating a current $CO_2$ level of the user by modeling a respiratory system of the user based on the at least one respiration signal.

13. The respiratory therapy device of claim 1, wherein the controller is configured to increase the flow rate supplied to the user from the first flow rate to the second flow rate to increase carbon dioxide flushing volume of lungs of the user by 5% to 15%.

14. The respiratory therapy device of claim 1 wherein the characteristic is a current $CO_2$ level.

15. A respiratory therapy device configured to supply a flow of breathable gas to a user via a breathing gas delivery conduit and a non-sealing patient interface to provide nasal high flow therapy, the device comprising:

a controller configured to control the flow of gas supplied to the user; and wherein the controller is configured according to a ramp cycle in which a flow rate of gases supplied to the user via the non-sealing patient interface is increased between first and second threshold flow rates over a determined number of breaths, the determined number of breaths selected responsive to a characteristic of a breathing pattern of the user, and in response to the second threshold flow rate being reached, the flow rate of the gases supplied to the user is rapidly decreased to the first threshold flow rate during an exhalation phase of one or more breaths.

16. The device of claim 15 wherein the ramp cycle has a saw tooth profile, gradually ramping upwards and then dropping sharply during the exhalation phase.

17. A method of providing respiratory therapy using a device configured to supply a flow of breathable gas to a user via a breathing gas delivery conduit and a non-sealing patient interface to provide nasal high flow therapy, the method comprising steps of:

using a controller of the device to control the device according to a variable ventilation profile to:

a) increase a flow rate of the breathable gas supplied to the user via the non-sealing patient interface from a first flow rate to a second flow rate over a number of breaths, wherein the number of breaths is selected responsive to a characteristic of a breathing pattern of the user; and b) in response to the second flow rate being reached or maintained for a predetermined period of time, decrease the flow rate of the breathable gas supplied to the user from the second flow rate to the first flow rate during one or more periods of exhalation.

* * * * *